(12) United States Patent
Cleveland et al.

(10) Patent No.: US 11,849,098 B2
(45) Date of Patent: Dec. 19, 2023

(54) GAZE-OPERATED POINT DESIGNATION ON A 3D OBJECT OR SCENE

(71) Applicant: Eyegaze Inc., Fairfax, VA (US)

(72) Inventors: Dixon Cleveland, Annandale, VA (US); Preethi Vaidyanathan, Fairfax, VA (US)

(73) Assignee: Eyegaze Inc., Fairfax, VA (US)

( * ) Notice: Subject to any disclaimer, the term of this patent is extended or adjusted under 35 U.S.C. 154(b) by 0 days.

(21) Appl. No.: 18/318,219

(22) Filed: May 16, 2023

(65) Prior Publication Data

US 2023/0370576 A1 Nov. 16, 2023

Related U.S. Application Data

(60) Provisional application No. 63/482,045, filed on Jan. 29, 2023, provisional application No. 63/364,777, filed on May 16, 2022.

(51) Int. Cl.
| | |
|---|---|
| H04N 13/117 | (2018.01) |
| G06F 3/01 | (2006.01) |
| G06T 7/70 | (2017.01) |

(52) U.S. Cl.
CPC .......... *H04N 13/117* (2018.05); *G06F 3/013* (2013.01); *G06T 7/70* (2017.01)

(58) Field of Classification Search
None
See application file for complete search history.

(56) References Cited

U.S. PATENT DOCUMENTS

| | | | |
|---|---|---|---|
| 2017/0003750 A1* | 1/2017 | Li | G06T 19/003 |
| 2017/0003764 A1* | 1/2017 | Li | G06F 3/04842 |
| 2017/0018121 A1* | 1/2017 | Lawson | G06V 40/10 |
| 2019/0199993 A1* | 6/2019 | Babu J D | G06F 3/011 |
| 2019/0381355 A1* | 12/2019 | Cooper | G06T 19/00 |
| 2020/0064911 A1* | 2/2020 | Mine | G06F 3/0304 |
| 2020/0326775 A1* | 10/2020 | Koo | G06T 7/521 |
| 2021/0333864 A1* | 10/2021 | Harvey | G06T 19/006 |
| 2022/0084296 A1* | 3/2022 | Sadalgi | G06T 15/50 |
| 2022/0269333 A1* | 8/2022 | Dedonato | G04G 9/0064 |
| 2022/0270509 A1* | 8/2022 | Josephson | G06F 3/0346 |
| 2022/0303272 A1* | 9/2022 | Ford | G06F 3/0482 |
| 2023/0074282 A1* | 3/2023 | Irie | G11B 27/031 |

\* cited by examiner

*Primary Examiner* — Talha M Nawaz
(74) *Attorney, Agent, or Firm* — Kasha Law LLC; John R. Kasha; Kelly L. Kasha

(57) ABSTRACT

A method for controlling the video display of a virtual 3D object or scene on a 2D display device is provided. A virtual video camera, controlled by a virtual-video-camera state variable consisting of camera control and location parameters, generates the 2D video of the object or scene. A target virtual camera state, representing an optimal view of a given surface point, is generated for each model surface point. A 2D coordinate of the image display is received from a user, either by looking at a point or selecting it with a mouse click. A corresponding 3D designated object point on the surface of the object is calculated from the received 2D display coordinate. The virtual camera is controlled to move its view toward the 3D designated object point with dynamics that allow the user to easily follow the motion of the designated object point as he watches the video.

8 Claims, 9 Drawing Sheets

US 11,849,098 B2

GAZE-OPERATED POINT DESIGNATION ON A 3D OBJECT OR SCENE

RELATED APPLICATIONS

This application claims the benefit of U.S. Provisional Patent Application Ser. No. 63/364,777, filed on May 16, 2022 and U.S. Provisional Patent Application Ser. No. 63/482,045, filed on Jan. 29, 2023, the content of all of which is incorporated by reference herein in their entireties.

INTRODUCTION

The teachings herein relate to using eyetracking to determine a point on a 3-dimensional (3D) virtual object shown on a 2-dimensional (2D) display. More particularly the teachings herein relate to systems and methods for designating a target point anywhere on a 3D surface of a virtual object or scene by looking at a time-varying 2D rendition of the 3D object or scene displayed on a video screen.

The systems and methods herein can be performed in conjunction with a processor, controller, or computer system, such as the computer system of FIG. 1.

Gaze-Based Pain Designation

Gaze-based pain designation refers to the process of determining a person's gazepoint on a 3D virtual object shown on a 2D display. Gaze-based pain designation is useful for people who are unable to use their hands or whose hands are occupied with other tasks and not available to manipulate the display. For example, an injured or disabled patient may wish to designate a point of pain on his body to an emergency medical technician at an accident scene or to a nurse/doctor in a hospital.

Conventional gaze-based pain designation methods generally consist of displays that enable the user to activate (or select or 'push') buttons displayed on the screen by visually fixating on them. Specifying a particular body location typically involves making a series of discrete selections. For example, the first display may be a set of 4 body views: front, back, and 2 sides. Subsequent displays provide an ever more focused selection among body parts.

Unfortunately, learning how to use these conventional methods is often difficult for patients. They require a cognitive understanding of the selection process. This means explicit instructions must be given and understood. In addition, even when learned, patients have a difficult time properly executing the methods. The discrete multi-step selection process is not intuitive for many patients.

As a result, additional systems and methods are needed for determining a person's gazepoint on a 3D virtual object shown on a 2D display, particularly in a medical setting.

BRIEF DESCRIPTION OF THE DRAWINGS

The skilled artisan will understand that the drawings, described below, are for illustration purposes only. The drawings are not intended to limit the scope of the present teachings in any way.

Figure 1:
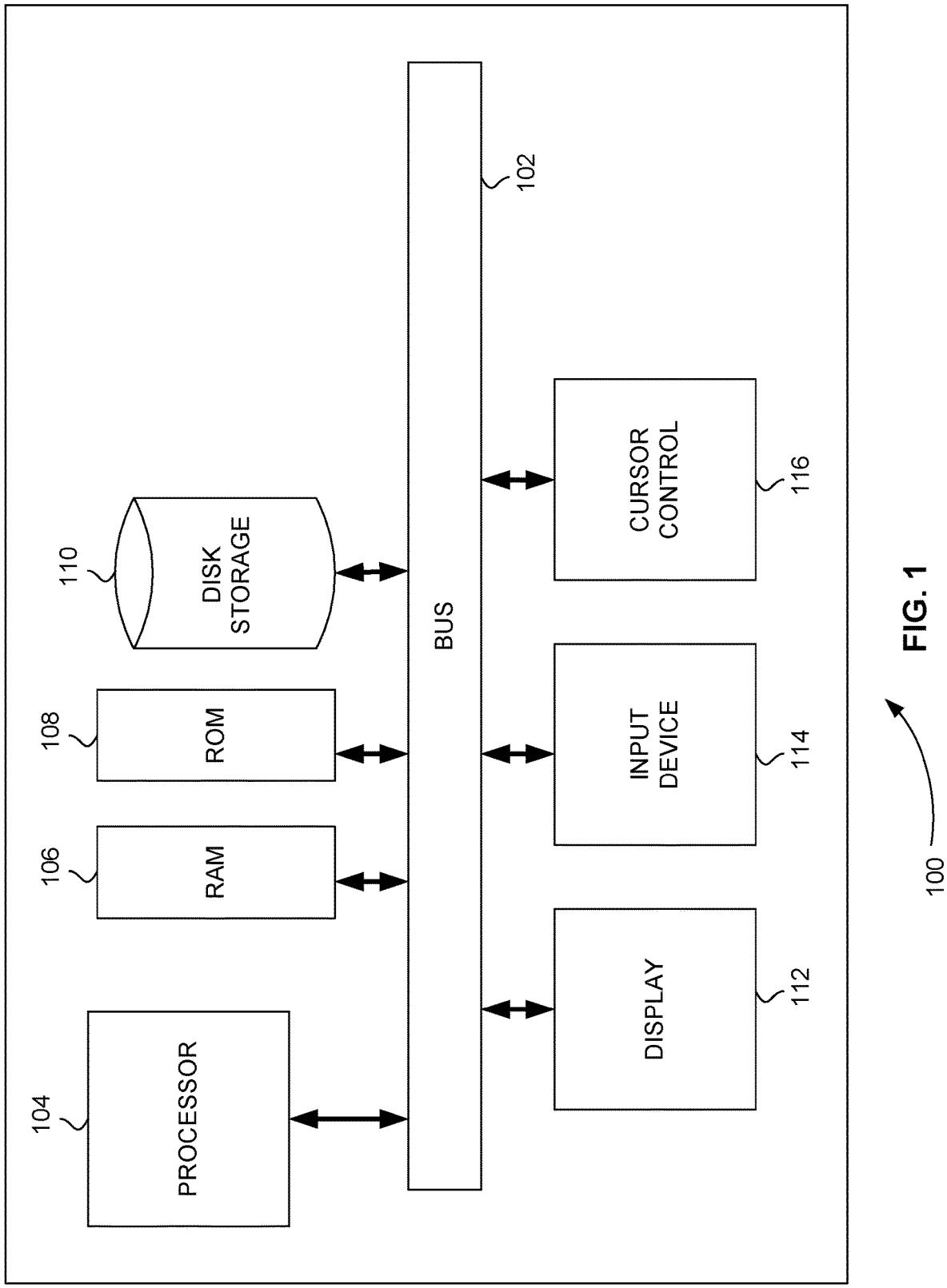
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random-access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112.

A computer system 100 can perform the present teachings. Consistent with certain embodiments of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein.

Alternatively, hard-wired circuitry may be used in place of or in combination with software instructions to implement the present teachings. For example, the present teachings may also be implemented with programmable artificial intelligence (AI) chips with only the encoder neural network programmed—to allow for performance and decreased cost. Thus, embodiments of the present teachings are not limited to any specific combination of hardware circuitry and software.

The term "computer-readable medium" or "computer program product" as used herein refers to any media that participates in providing instructions to processor 104 for execution. The terms "computer-readable medium" and "computer program product" are used interchangeably throughout this written description. Such a medium may take many forms, including but not limited to, non-volatile media and volatile media. Non-volatile media includes, for example, optical or magnetic disks, such as storage device 110. Volatile media includes dynamic memory, such as memory 106.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. The computer-readable medium is accessed by a processor suitable for executing instructions configured to be executed.

The following descriptions of various embodiments of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described embodiment includes software but the present teachings may be implemented as a combination of hardware and software or in hardware alone. The present teachings may be implemented with both object-oriented and non-object-oriented programming systems.

Gaze Operated Point Designation (GOPD)

As described above, gaze-based pain designation refers to the process of determining a person's gazepoint on a 3D virtual object shown on a 2D display. Conventional gaze-based pain designation methods generally consist of displays that enable the user to activate (or select or 'push') buttons displayed on the screen by visually fixating on them. Unfortunately, learning how to use these conventional methods is often difficult for patients.

As a result, additional systems and methods are needed for determining a person's gazepoint on a 3D virtual object shown on a 2D display, particularly in a medical setting.

In various embodiments, Gaze Operated Point Designation (GOPD) is a significant improvement over conventional gaze-based pain designation methods. GOPD is easier for patients to learn and use. GOPD refers to the process of determining a person's gazepoint on a 3D virtual object shown on 2D display and adjusting the 3D virtual object in response to that determination.

The following non-limiting example illustrates some key steps of GOPD. In this example, the patient is presented with a general display of a human body on a computer screen and asked where on his body he is experiencing the most pain. The patient, for example, has a ruptured right Achilles tendon.

A computer driving the GOPD display contains a Virtual 3D Model of the surface of a typical human body. The 3D model might, for example, be a mesh/grid surface, where a set of 3D coordinates specify points on the 3D body surface, and each triplet set of neighboring points describes a plane that has a normal vector defining a perpendicular to the body surface over the corresponding triangular area.

At any point in time, the system presents the patient with a 2D perspective of the 3D human-body model, as would be seen by a Virtual Video Camera in the vicinity of the body. As the Virtual Video Camera translates (i.e. shifts position) and rotates around the body, the display of the body shifts and reorients accordingly.

Initially, the system can portray a frontal view of the full body, with the center of the stomach located at the center of the display screen. (The Virtual Video Camera state that provides this initial stomach-center point and frontal perspective is arbitrary.)

After initially glancing all around the screen to recognize that he is observing a human body, the patient then looks toward the right lower leg. Since the Achilles tendon is not directly visible in the display at this point, he naturally looks at a point on the body near the tendon.

The system, using an eyetracker, determines where on the display the patient is looking. The eyetracker, using, for example, a video camera observing the patient's eyes, measures his 2D gaze coordinate on the screen. The system determines, based on its geometric knowledge of the body rendition it is currently displaying, that the patient's 2D gaze coordinate on the screen corresponds to a specific 3D body point, or Object Gazepoint, on his lower right leg.

The system begins to shift the display so that the Object Gazepoint (i.e. the point on his lower right leg) begins to move toward the center of the screen. In GOPD systems, this screen center point is more generally termed the Home Pixel, i.e. the point on the display where the user's object point of interest finally settles. Typically, the Home Pixel is highlighted on the display to provide the user and outside observers with a visual reference point. As the body image shifts within the display, the patient's gaze naturally follows his point of interest in the body image.

As the image of the lower leg and patient gazepoint simultaneously approach the Home Pixel, the GOPD system begins to zoom the image, providing an expanded view of the lower leg and allowing the gaze tracker to more precisely determine the patient's Designated Object Point of interest. Nominally, if the user's gazepoint remains moderately fixed on a single point on the 3D Object, the GOPD system increases its zoom over time. On the other hand, if the user's gazepoint varies significantly around the object surface, the system zooms back out.

A key operational feature at this point is that the GOPD system, given its internal 3D model of the body surface, notes that the gazepoint intercepts the body along a perspective line that is not perpendicular to the local body surface at that point. For example, if the gazepoint is on the right side of the patient's leg, the perpendicular line from that point on the leg no longer projects directly forward from the body (as did the original projection from the center of the stomach). The perpendicular line from the right side of the leg now projects more to the body's right.

In response to the new perpendicular direction at that point on the body, the position and orientation of GOPD's Virtual Video Camera automatically translate and rotate to align the camera's perspective view of the body with the body perpendicular at that body point. This camera shift begins to bring the Achilles tendon, which was not directly displayed in the original body presentation, into view, now allowing the patient to look at directly it.

As the patient keeps his gaze on the tendon, the display view automatically continues to reposition, rotate and zoom until the display presents a direct, centered and zoomed view of the tendon at the Home Pixel.

The camera repositioning, rotation and zoom control loops operate iteratively, for example, at each iteration sample: measuring the current gazepoint (including both the 2D gaze coordinate on the display screen and the corresponding 3D gazepoint on the 3D object), and adjusting/driving the state of the Virtual Video Camera in accordance with the current gazepoint.

A Camera Trajectory Control function continues to reposition, rotate and zoom the Virtual Video Camera presentation until the following steady state condition is reached: the image of the Designated Object Point, reaches the Home Pixel, the 3D orientation of the display presents a prescribed, typically approximately straight on, view of the designated body part, and the Zoom Condition has reached a prescribed value. The GOPD's Zoom Condition is defined by the amount (e.g. width) of the Virtual 3D Object that is seen in the Virtual Video Camera image and displayed to the user.

When all the above steady state conditions are met, the object motion displayed in the display window slows to a stop, indicating that the patient has designated his desired point of interest. At this point, it is clear to both the patient, who is looking at his own display window, and to his caregivers and others who may have their own display devices mirroring the patient's display window, precisely what point on the body the patient wishes to designate.

Figure 2:
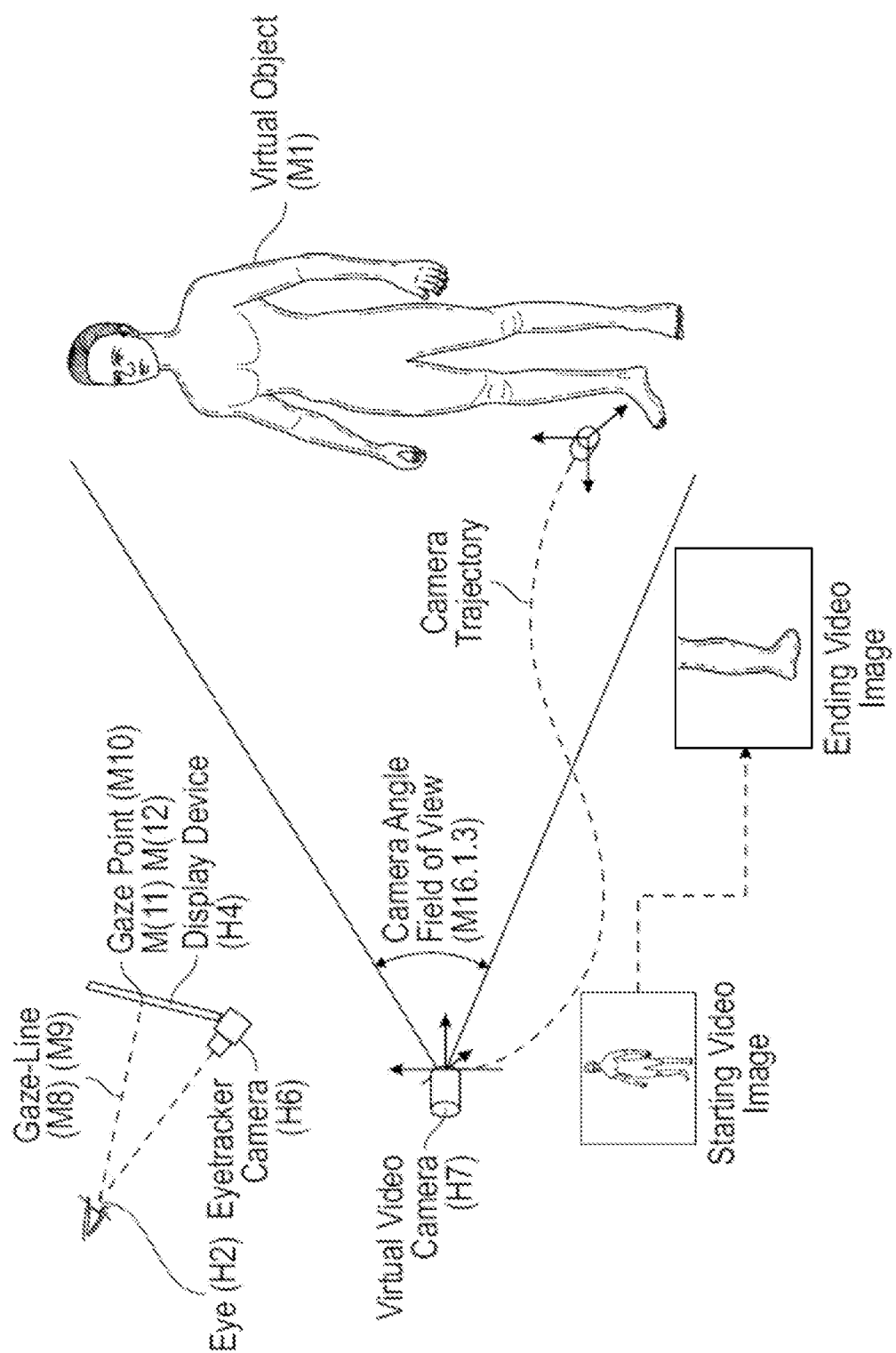
FIG. 2 is an exemplary diagram showing the trajectory of the Virtual Video Camera with respect to the body in the PainPoint example of a GOPD application, and it shows the camera images with their respective Zoom Conditions at the beginning and end of the camera trajectory, in accordance with various embodiments.

FIG. 2 is an exemplary diagram 200 showing the trajectory of the Virtual Video Camera with respect to the body in the PainPoint example of a GOPD application, and it shows the camera images with their respective Zoom Conditions at the beginning and end of the camera trajectory, in accordance with various embodiments. FIG. 2 shows the Virtual Video Camera (H7) moving from its original full frontal body view to its zoomed direct view of the right Achilles tendon.

A significant advantage of this gaze-driven point designation procedure is that the user's eye activity involved in following his point of interest—i.e. visual smooth pursuit—is a deeply natural human behavior. People innately look at and visually follow what they are interested in. This behavior does not need to be taught to or newly learned by a novice eyetracker user. He just does it automatically. The user need not even consciously know that his eye activity is controlling the display, or that his eyes are even being tracked. The feature is particularly valuable in emergency or critical-care medical situations, where the patient's conscious attention is on his physical condition, not how to operate the eyetracking device that is helping communicate that condition to his caregivers.

In various embodiments, GOPD can be used for medical diagnosis. Pain is the most common diagnostic symptom of traumatic injury patients at accident scenes, in the emergency room (ER) and in the intensive care unit (ICU). Also, most critically ill patients experience pain at multiple locations of their body. Pain assessment poses significant challenges, especially for patients who possess valuable diagnostic information about their condition but cannot communicate it effectively because they are not able to speak, write or otherwise signal their thoughts. As a result, pain frequently goes undetected or is incorrectly diagnosed, and treatment is either insufficient or excessive. Diagnostic errors often result in less effective medical outcomes and costly extended hospital stays.

The patient's self-report of pain and its location is the most accurate and dependable source for pain assessment. Due to their medical condition, however, critically ill patients often cannot accurately self-report pain to their caregivers. When a patient is non-communicative, healthcare providers usually rely on nonverbal signs like facial expressions and gestures to recognize pain. These nonverbal clues do not indicate exactly where the patient is hurting. Also, not all nonverbal cues indicate that the patient is in pain; some could indicate discomfort, anxiety, agitation, or other factors that further complicate the communication between the patient and healthcare personnel, presenting unacceptable risk factors.

The GOPD pain assessment system, herein called the PainPoint application, enables patients to communicate a pain point to their healthcare providers without having to speak or manually point to it. The system displays a computer-generated, three-dimensional representation of a human body, allowing patients to define the location of pain simply by looking at the point on the display. The approach utilizes the human eye and brain's inherent instinct to look at the problem point. To provide precise pain location capability, the system dynamically zooms in on the part of the body the patient is looking at, ultimately positioning the image of the pain point at the Home Pixel for both patient and caregiver to see.

With improved pain diagnostic information, healthcare providers formulate and execute more effective treatment plans and are better able to monitor the progress of these plans. The ultimate result is reduced diagnostic error, better medical outcomes, reduced hospital costs and improved patient satisfaction.

A GOPD-based pain diagnostic represents a significant improvement over today's conventional gaze-based pain designation methods, which generally consist of displays that enable the user to activate (or select or 'push') buttons displayed on the screen by visually fixating on them. Specifying a particular body location typically involves making a series of discrete selections. For example, the first display may be a set of 4 body views: front back and 4 sides. Subsequent displays provide ever more focused selection among body parts.

The GOPD method provides several advantages with respect to the above sequential selection method. The GOPD method: (1) Takes advantage of the brain/eye's natural smooth pursuit behavior of tracking a target of interest, (2) Requires less explicit cognitive understanding of the selection process, allowing new eyegaze users to operate the system with no or only very little direction. (3) Provides a continuous rather than discreet-step selection procedure, making the process easier to execute. (4) Provides more precise point designation, and (5) Has a more natural way of backing up if the user wants to make a correction.

The GOPD PainPoint application is an improvement over the EyeVoice patient communication system described in U.S. Pat. No. 9,244,528, Gaze Based Communications for Locked-In Hospital Patients, Cleveland, N. et al, included here in its entirety. In essence, "EyeVoice allows hospital patients who cannot speak or gesture to communicate with their care givers using their eyes in place of their voices. Simply by looking at images and cells displayed on a computer screen placed in front of them, patients are able to: answer questions posed by caregivers; specify locations, types and degrees of pain and discomfort; request specific forms of assistance; ask or answer care related questions; and help direct his own care. The GOPD PainPoint application provides a more natural and precise method for designating pain points."

In various embodiments, an operational goal of GOPD systems is to allow a person to designate a specific point of interest, here called the Designated Object Point, anywhere on the surface of a complex 3D object based on the natural viewing activity of his eyes alone. Based on a person's intrinsic instinct to look at a point of interest to him, the GOPD system employs an eyetracking device to measure where on the display the user is looking, and consequently what part of the object the person is looking at, and then automatically adjusts the displayed view of the object to move the image of the designated object point to a Home Pixel on the display. The display's Home Pixel is often the center point of the GOPD's display window.

The display device is a 2D screen that presents a time varying 2D view of a 3D object. The GOPD's time-varying display adjustments include: the 3D rotation, or angular orientation, of the Virtual Video Camera, so that the display presents a clear, direct view of user's Designated Object Point of interest, the shifting, i.e. translation, of the object display so the image of the Designated Object Point moves to the window Home Pixel, and the zoom of the object display, so that the specificity of the Designated Object Point is sufficiently accurate for the GOPD system purpose.

Note that, though this specification discusses the GOPD display in terms of a Virtual Video Camera moving around a Virtual 3D Object, an alternative embodiment where the Virtual 3D Object moves with respect to the Virtual Video Camera is functionally equivalent.

Figure 3:
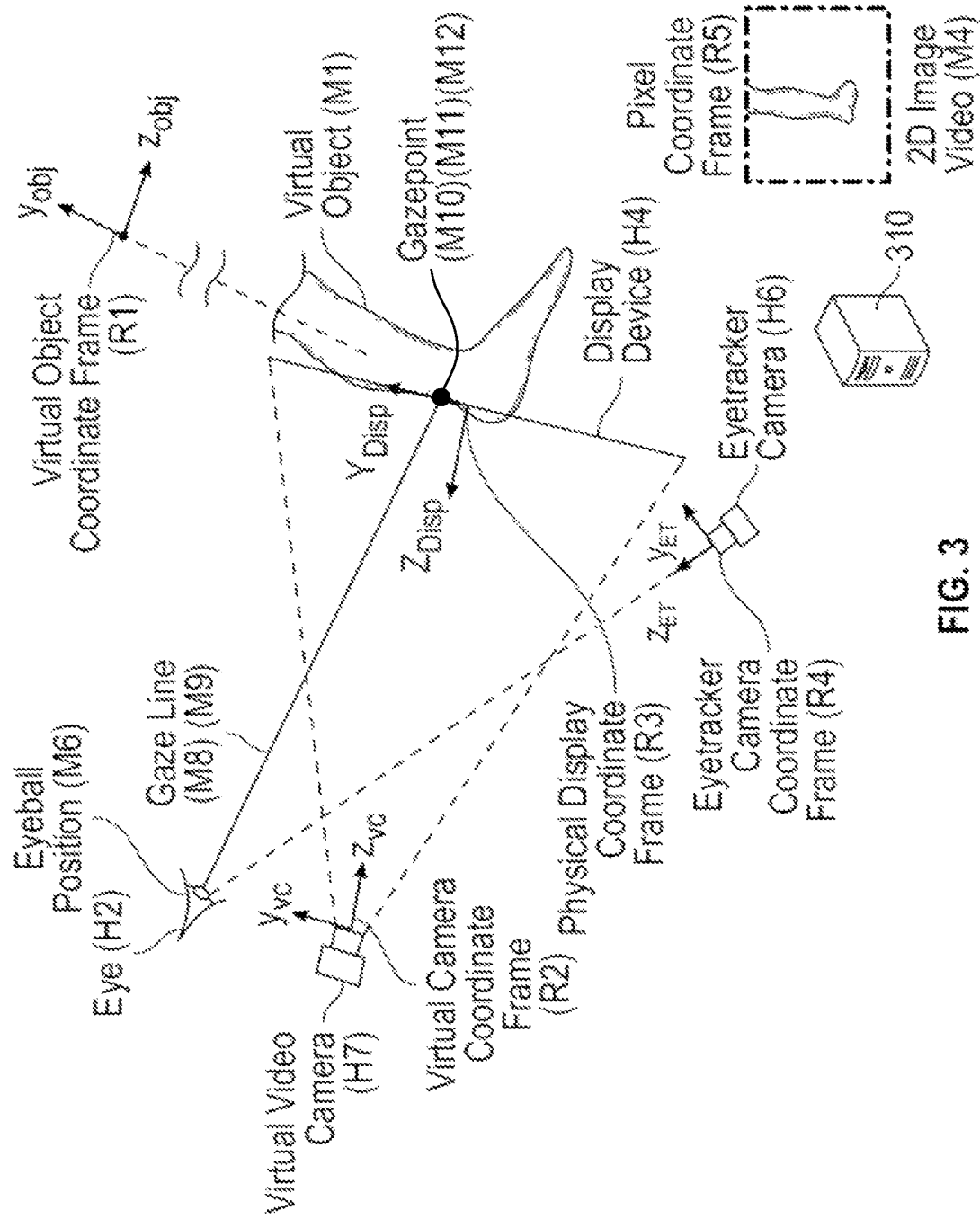
FIG. 3 is an exemplary diagram showing an abstract view of the spatial geometry of several different real and virtual elements of a GOPD system, along with the locations and orientations of relevant spatial frames of reference, in accordance with various embodiments.

FIG. 3 is an exemplary diagram 300 showing an abstract view of the spatial geometry of several different real and virtual elements of a GOPD system, along with the locations and orientations of relevant spatial frames of reference, in accordance with various embodiments. The Virtual 3D Object ($S_{Obj\_Obj}$) (M1), Virtual Video Camera (H7), Display Device (H4), Eyetracker Camera (H6), Eyeball Position (M6), the Gaze Line (M8 and M9), and the Gazepoint (M10, M11, and M12) all exist within different coordinate frames, requiring coordinate transformation functions to convert position and orientation data between different coordinate frames. Virtual 3D Objects (M1) may spatially overlap real objects. In the drawing, the Eye (H2) and the Virtual Video Camera (H7) are shown separately for clarity, but often overlap in practice. The x axes of all coordinate systems, not shown in the figure, go either into or out of the page. Note that FIG. 3 uses the foot of the GOPD PainPoint application as an example of the Virtual 3D Object (M1) being displayed.

Figure 4:
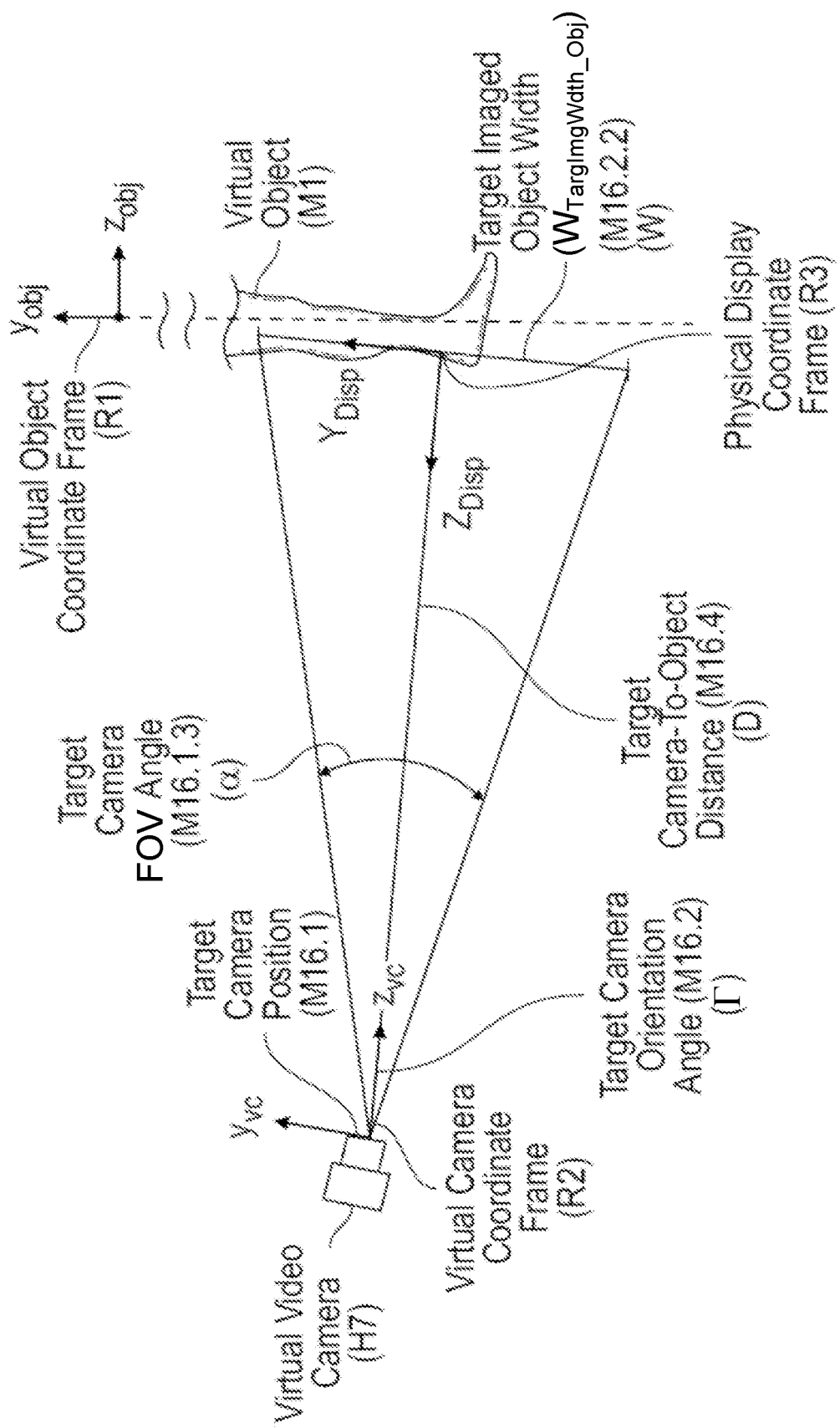
FIG. 4 is an exemplary diagram showing the geometry for computing the Target Camera State ($C_{TargCam\_Obj}$) (M21) for a given the Designated Object Point ($P_{DesigPt\_Obj}$) (M13), in accordance with various embodiments.

FIG. 4 is an exemplary diagram 400 showing the geometry for computing the Target Camera State ($C_{TargCam\_Obj}$) (M21) for a given the Designated Object Point ($P_{DesigPt\_Obj}$) (M13), in accordance with various embodiments. Specifically, FIG. 4 shows the geometric relationships between the following GOPD variables and coordinate frames: the Virtual Object Coordinate Frame (R1), Virtual Camera Coordinate Frame (R2), and Physical Display Coordinate Frame (R3), the target Camera Position ($P_{Targ\_Cam\_Obj}$) (M21.1.1) in the Virtual Object Coordinate Frame (R1), the target Camera Orientation Angle ($Tr_{TargCam\_Obj}$) (M21.1.2) in the Virtual Object Coordinate Frame (R1), the target Camera FOV Angle ($\alpha_{TargCamFOV}$) (M21.1.3), i.e. the Virtual Video Camera's (H7) angular field-of-view control setting, the target Camera-To-Object Distance ($D_{TargCamToObjDist}$) (M21.2.1), i.e. the distance of the Virtual Video Camera (H7) from the Designated Object Point ($P_{DesigPt\_Obj}$) (M13) on the surface of the Virtual 3D Object ($S_{Obj\_Obj}$) (M1), and the target Imaged Object Width ($W_{TargImgWdth\_Obj}$) (M21.2.2), i.e. the linear length of the Virtual 3D Object seen across the width of the camera image.

Figure 5:
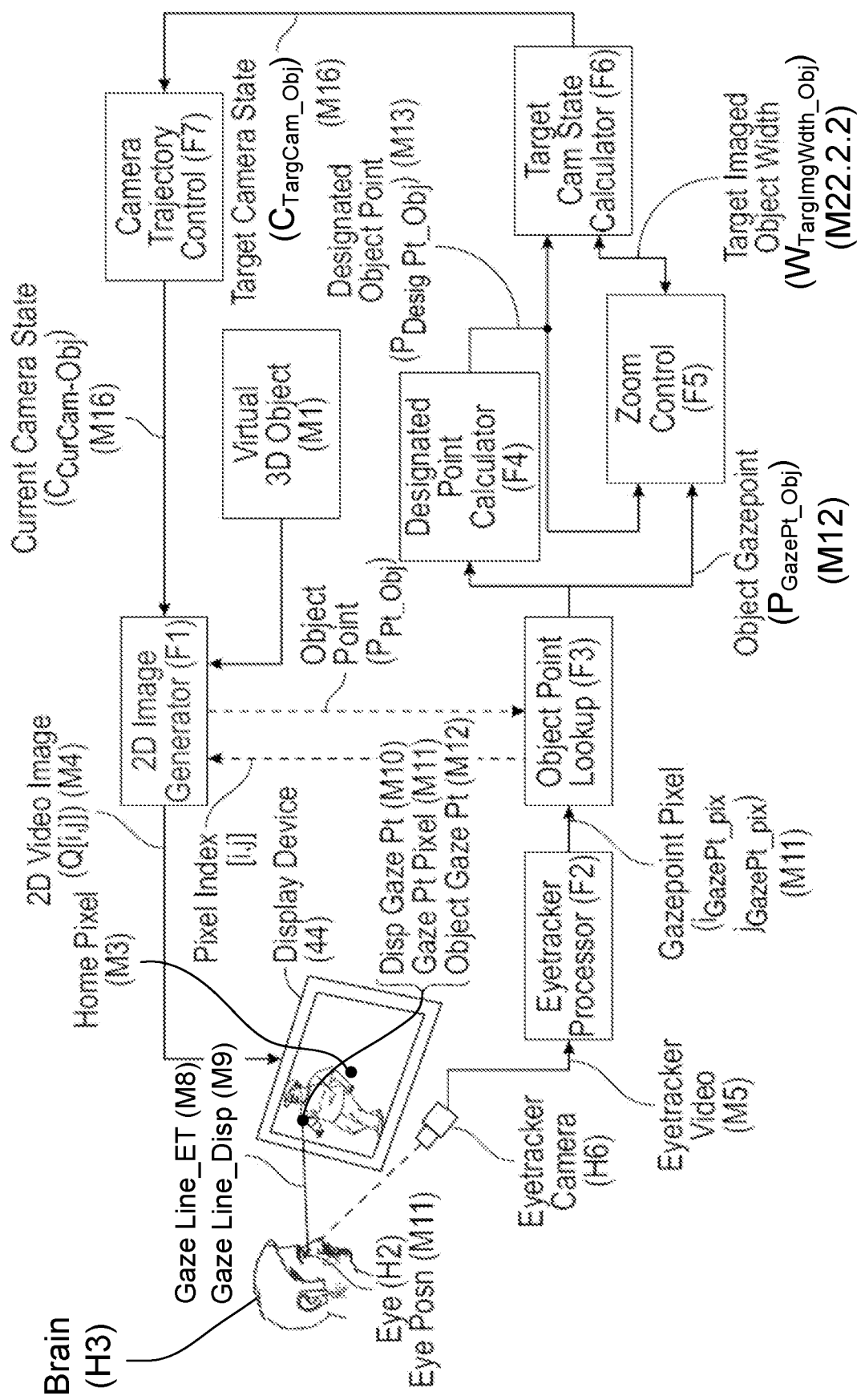
FIG. 5 is an exemplary diagram showing the functional flow of the GOPD system's main outer Eye Control Loop loop, in accordance with various embodiments.

FIG. 5 is an exemplary diagram 500 showing the functional flow of the GOPD system's main outer Eye Control Loop loop (L1), in accordance with various embodiments. FIG. 5 shows the User observes the motion of the Virtual 3D Object ($S_{Obj\_Obj}$) (M1) as it is currently displayed on the Display Device (H4), the Eyetracker Camera (H6) monitors the User's Eyes (H2) to produce the Eye Video (M5), the Eyetracker Processor function (F2) processes the Eyetracker Video (M5) to compute the Eyeball Position_ET ($P_{Eye\_Et}$) (M6), Gaze Direction Vector_ET ($V_{GazeDir\_Et}$) (M7), the Gaze Line_ET ($L_{GazeLine\_Et}$) (M8), the Gaze Line_Disp ($L_{GazeLine\_Disp}$) (M9), the Display Gazepoint ($P_{GazePt\_Disp}$) (M10), and the Gazepoint Pixel (M11) within the Eyetracker Camera Coordinate Frame (R4) (FIG. 6 shows more detail of the Eyetracker Processor function (F2)), the Object Point Lookup function (F3) processes the Gazepoint Pixel (M11) to compute the User's Object Gazepoint ($P_{GazePt\_Obj}$) (M12) on the displayed portion of the Virtual 3D Object ($S_{Obj\_Obj}$) (M1), the Designated Object Point Calculator function (F4) calculates the User's Designated Object Point ($P_{DesigPt\_Obj}$) (M13) from the recent history of the User's Object Gazepoint ($P_{GazePt\_Obj}$) (M12), the Zoom Control function (F5), sets the current GOPD zoom condition (more particularly the target Imaged Object Width ($W_{TargImgWdth\_Obj}$) (M21.2.2)) from the current Designated Object Point ($P_{DesigPt\_Obj}$) (M13) and his recent Object Gazepoint history ($P_{GazePt\_Obj}$) (M12) across the Object, the Target Camera State Calculator function (F6) computes the Target Camera State ($C_{TargCam\_Obj}$) (M21) from the User's Designated Object Point ($P_{DesigPt\_Obj}$) (M13) and the target Imaged Object Width ($W_{TargImgWdth\_Obj}$) (M21.2.2), the Camera Trajectory Control function (F7) controls the trajectory of the Virtual Video Camera (H7) to move toward the Target Camera State ($C_{TargCam\_Obj}$) (M21), the 2D Image Generator function (F1) computes the next frame of the 2D Video Image (Q[i,j]) (M4) based on the next state of the Actual Camera State ($C_{ActCam\_Obj}$) (M17), and the Display Device (H4), displays the next 2D Video Image frame (Q[i,j]) (M4).

FIG. 5 includes the following operation functions.
(F1) 2D Image Generator function.
(F1.1) GetPixelColor function.
(F1.2) GetPixelObjectPosition function.
(F2) Eyetracker Processor functions. (See FIG. 6)
(F2.1) Eye Image Processor function.
(F2.2) Gaze Line Calculator function.
(F2.3) Compute Gaze-Line/Display-Surface Intercept function.
(F3) Object Point Lookup function.
(F4) Designated Object Point Calculator function.
(F5) Zoom Control function.
(F6) Target Camera State Calculator function.
(F7) Camera Trajectory Control function. (See FIG. 7)
(F8) GOPD Coordinate Transformation functions: (F8.1) 3D Coordinate Transformation function, (F8.2) Display-To-Pixel Transform function,
(F9) Adjust Zoom Limit function, and
(F10) Set Target Camera Control Parameters function.

Figure 6:
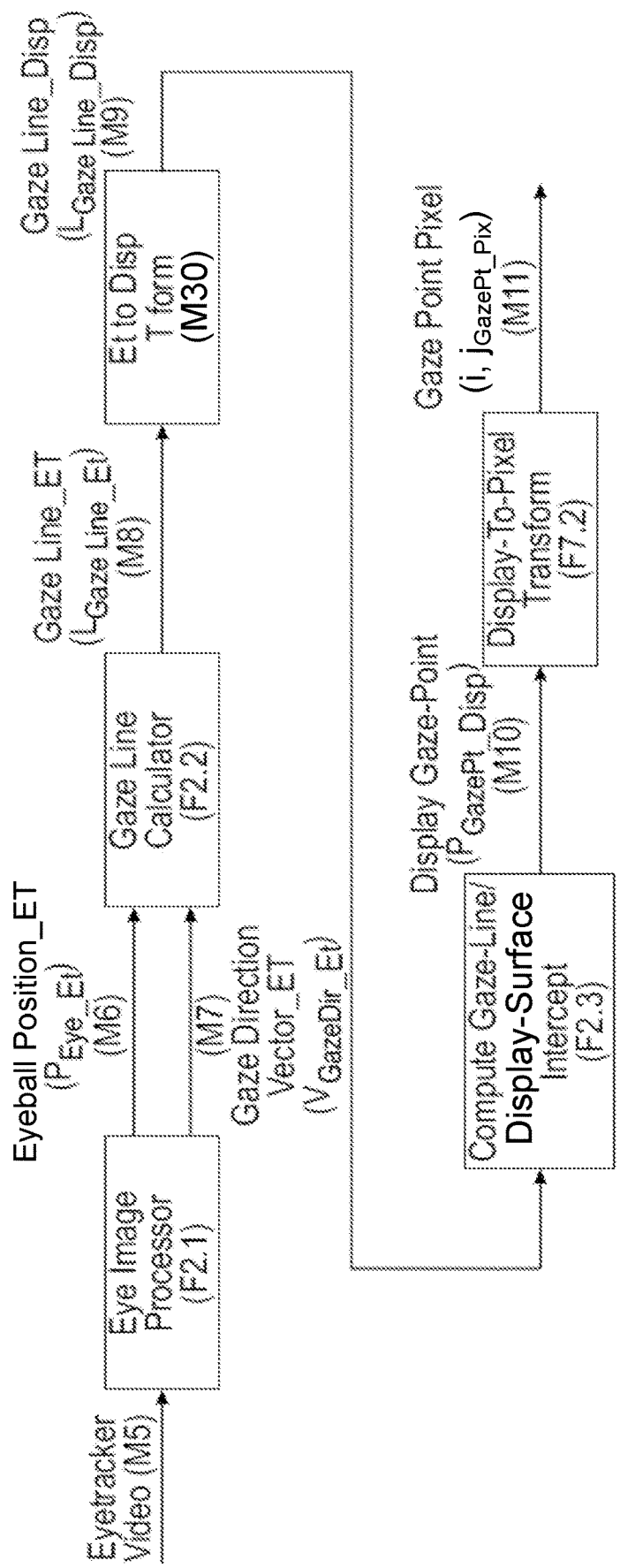
FIG. 6 is an exemplary diagram showing the method of the Eyetracker Processor function (F2) method, in accordance with various embodiments.

FIG. 6 is an exemplary diagram 600 showing the method of the Eyetracker Processor function (F2) method, in accordance with various embodiments.

Figure 7:
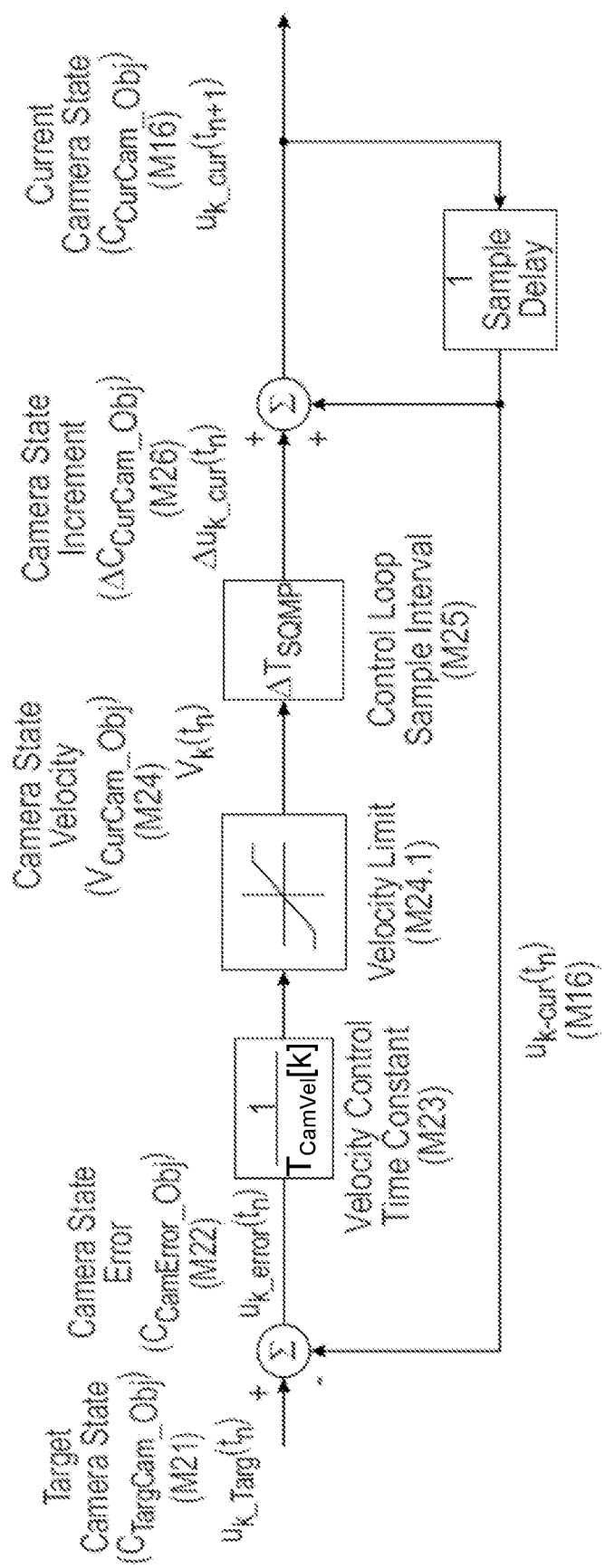
FIG. 7 is an exemplary diagram showing the Camera Trajectory Control function (F7) method, in accordance with various embodiments.

FIG. 7 is an exemplary diagram 700 showing the Camera Trajectory Control function (F7) method, in accordance with various embodiments.

In various embodiments, five key fields of physiology and engineering discipline underlie the practical embodiment of GOPD. First, the Eye/Brain System is the naturally existing human component of the GOPD system. As discussed earlier, a key physiological function of the human brain is to control the gaze activity of its eyes. As the brain executes a high-level task involving visual information, it continually directs its eyes toward the item or activity in the environment that is most important to the accomplishment of its task. GOPD is built around this natural human brain behavior to direct its eyes toward the information most useful to it at any time. Given the task of visually designating a point of interest, the brain will naturally keep its eyes pointed at that point as the display changes. This behavior does not need to be taught. It is an innate, natural and automatic activity. (This eye/brain behavior exists in almost all animals that have eyes, so GOPD systems have potential application beyond humans.)

In the dynamic phase of GOPD operation, the view of the displayed object is continually shifting, rotating, and zooming—as if a Virtual Video Camera (H7), representing the user's own eyes, were moving around the object. A critical eye behavior during this activity is smooth visual pursuit, where the brain naturally controls the eye's gaze to follow a moving object of interest. Based on the eye/brain's smooth-pursuit behavior, the GOPD's display system adjusts the view of the object under the assumption that the user keeps his gaze pointed at his Designated Object Point of interest. At the same time, however, the rates of the GOPD's presentation change should be matched to comfortable tracking speeds that the eye/brain behavior easily accommodates. The presentation adjustment speeds should be slow enough for the eye/brain system to follow easily but rapid enough to complete the GOPD convergence process quickly without losing the user's visual attention. As discussed below, a key purpose of the GOPD control system is to match the overall GOPD system convergence speeds to natural eye/brain smooth pursuit speeds.

Second, Eyetracking Technology enables GOPD systems to automatically measure a person's direction of gaze in real-time. In particular, for GOPD applications, an Eyetracker Device is used to measure the user's gazepoint on its 2D display device's active screen.

Eyetrackers (including gazepoint trackers) can take many forms, including mechanical, galvanic, and video oculography. Video eyetrackers are the preferred type for GOPD systems due to their higher gazepoint tracking accuracy. A video eyetracker in a GOPD system, for example, typically consists of: a video camera to view the user's eye or eyes, video eye-image processing software to detect the eyes in the camera video stream, measure the eyeball position, and measure the direction of eye's gaze line, and gazepoint measurement means to calculate the gazepoint coordinate where the eye's gaze line intercepts the 2D display device's active screen area.

Third, GOPD systems employ modern Graphics Technology, 3D rendering in particular, to enable the dynamic, realistic display of virtual objects in real time. The GOPD's Graphics Display System simulates a Virtual Video Camera (H7) moving around within the Virtual-Object Coordinate Frame (R1)—automatically modifying its angular orientation, spatial position and zoom condition to present an optimal view of the user's visually Designated Object Point. Current graphics technology nicely supports real-time 2D display of 3D objects as viewed from a moving point of view.

GOPD systems utilize the modern graphics concept of a digital twin. The GOPD's Virtual 3D Object variable ($S_{Obj\_Obj}$) (M1), is a digital twin, forming the system's internal representation of an object or scene to be viewed by the User.

Fourth, the Field of Feedback Control provides basic conceptual methods for achieving stable, predictable operation of the GOPD's dynamic performance goals.

As noted earlier, the central GOPD goal is to give the user control of his view of the Virtual 3D Object ($S_{Obj\_Obj}$) (M1) simply by looking at his point of interest. In a preferred GOPD embodiment, the view is generated as if a Virtual Video Camera (H7) were moving around in space under the user's control. The simulated Virtual Video Camera (H7) starts off at an arbitrary distant point, pointed at or near the center of the object or scene, and with a field of view wide enough to include the entire object. The camera then starts: rotating its angular orientation toward the user's Designated Object Point ($P_{DesigPt\_Obj}$) (M13), swinging (i.e. translating) its position around the Virtual 3D Object ($S_{Obj\_Obj}$) (M1) to get the best perspective view of the Designated Object Point ($P_{DesigPt\_Obj}$) (M13), and zooming in and out to provide more detail or a wider field of view.

GOPD systems use two nested control loops: an outer Eye Control Loop (L1) and an inner Camera Trajectory Control Loop (L2). The outer Eye Control Loop comprises all the functions shown in FIG. 5. The inner Camera Trajectory Control Loop is executed by the Camera Trajectory Control function (F7) which is shown in more detail in FIG. 7.

Both the outer Eye Control Loop and the inner Camera Trajectory Control Loop are considered to be "classical" feedback control systems, wherein each loop:

a. has a plant, i.e. a dynamic process, which the loop controls,
b. has a measured controlled variable, i.e. a primary variable in the plant, that the loop controls,
c. is provided an input setpoint or command value that the controlled variable is supposed to follow,
d. computes an explicit error signal that is the difference between the setpoint and the controlled variable, and
e. takes continual action within the scope of its loop to correct the error, i.e. to smoothly and stably drive the error to zero, despite any incoming changes in the setpoint.

The plant that the GOPD's Outer Eye Control Loop (L1) controls is comprised of two key subsystems:
a. the moving Virtual Video Camera (H7) that views and displays the Virtual 3D Object ($S_{Obj\_Obj}$) (M1), and
b. the human User watching the Virtual Video Camera's (H7) 2D Video Image (Q[i, j]) (M4) of the Virtual 3D Object ($S_{Obj\_Obj}$) (M1).

The error in the GOPD's Outer Eye Control Loop (L1) is defined to be the difference between the Designated Object Point ($P_{DesigPt\_Obj}$) (M13) (the setpoint) where the user is looking and the Object Home Point ($P_{HomePt\_Obj}$) (M27) (the controlled variable) where the camera is currently actually pointing. The Outer Eye Loop Controller (L1) takes the action of telling the Inner Camera Trajectory Control Loop (L1) the Target Camera State ($C_{TargCam\_Obj}$) (M21) that the camera should ultimately assume if the current Designated Object Point ($P_{DesigPt\_Obj}$) (M13) were to remain constant at its current value.

The plant that the GOPD's Inner Camera Trajectory Control Loop (L2) controls is a simulated Virtual Video Camera Platform (H7.1) that 'manipulates' the current Actual Camera State ($C_{ActCam\_Obj}$) (M17) of Virtual Video Camera (H7) through the Camera Trajectory Control function (F7). A key feature of the GOPD invention is the implementation of appropriate Virtual Video Camera Platform (H7.1) dynamics that enable and enhance the Eye/Brain's natural smooth-pursuit behavior to visually follow a point of interest on a moving object.

The error for the Inner Camera Trajectory Control Loop (L2) is the Camera State Error ($C_{CamError\_Obj}$) (M22), i.e. the difference between the Target Camera State ($C_{TargCam\_Obj}$) (M21) (the setpoint) and the Actual Camera State $C_{ActCam\_Obj}$) (M17) (the controlled variable). The action of the inner Camera Trajectory Control Loop is to manipulate the activity of the Virtual Video Camera (H7) such that the 2D Video Image display (Q[i,j]) (M4) of the Virtual 3D Object (M1) behaves in a manner that allows the human brain and its vision system to either:
a. use its smooth pursuit capability to comfortably follow the resulting path of the Designated Object Point ($P_{DesigPt\_Obj}$) (M13) within the Object Display, and/or
b. use its saccadic behavior to jump to alternative points of interest on the Object, much as it would observe, evaluate and interpret the activity of other moving objects in its natural environment.

As can be seen from the above control-loop discussion, the implementation of the plants in the GOPD's inner and outer control loops (L1 and L2) are unique components of GOPD systems; they are not typical physical systems for which control systems are traditionally designed. At the same time, conventional control system design principles are directly applicable to optimal and stable GOPD control loop implementations.

Fifth, GOPD systems utilizes Computer Technology to execute the mathematical algorithms used throughout the system, including: the eyetracking; designated object point calculation; target camera state calculation; Virtual Video Camera (H7) simulation and control; and graphics generation and presentation. As is well known in the art, computer processors typically contain the memory (including read only memory (ROM), random access memory (RAM), and/or other dynamic storage), communication (including internal bus communication devices, and externally connected input/output (I/O) devices), and processing capabilities (including central processing units (CPUs) arithmetic processors and graphics processors) needed to execute the GOPD's programmed algorithms.

GOPD Elements

A preferred embodiments for GOPD systems includes the following human, hardware, functional, geometrical and mathematical elements.

{Notation Notes: The 'H' notation (Hx) designates physical human anatomical elements and hardware equipment. The 'F' notation (Fx) designates GOPD computational functions, executed by computer hardware. The 'L' notation (Lx) designates key GOPD feedback control loops. The 'R' notation (Rx) designates spatial coordinate frames of reference relevant to GOPD operation. The 'M' notation (Mx) designates mathematical elements used in the computational functions. Mathematical elements often include an abbreviated variable name (in parentheses) for clarity.}

Key GOPD Human and Equipment Hardware Elements

In various embodiments, GOPD includes the following elements.

(H1) The Human User is the person operating the GOPD system.
(H2) The Eye is the User's eye or eyes which observe the 2D Video Image (Q[i,j]) (M4) displayed on the Display Device (H4). (See Note 1 at the end of the GOPD Variables list for a discussion of 'eye' vs 'eyes.')
(H3) The Brain indicates the User's brain which directs the fundamental GOPD operation by:
a. processing the visual data produced by the Eye,
b. establishing a point of interest on the GOPD's displayed Object, and
c. pointing the Eye at the point of interest on the displayed image.
(H4) The Display Device is the physical device that presents the 2D Video Image (Q[i,j]) (M4) of the Virtual 3D Object ($S_{Obj\_Obj}$) (M1) to the User. The Display Device (H4) typically (though not necessarily) consists of a flat 2D grid of pixels (picture elements) which are indexed by the display device's pixel coordinate (i, j).
Note: The 2D Video Image (Q[i,j]) (M4) may be displayed over the Display Device's
(H4) full 2D pixel grid or within a portion of the grid. The pixel region over which the 2D Video Image (Q[i,j]) (M4) is displayed is called the Display Window (H4.1).
(H5) The Eyetracker Device is the instrument that observes the Eye (H2) with its Eyetracker Camera (H6) and computes the following variables from the Eyetracker Video (M5) in its Eyetracker Processor function (F2): the Eyeball Position_ET ($P_{Eye\_Et}$) (M6), expressed in the Eyetracker Camera Coordinate Frame (R4); the Gaze Direction Vector_ET ($V_{GazeDir\_Et}$) (M7), expressed in the Eyetracker Camera Coordinate Frame (R4); the Gaze Line_ET ($L_{GazeLine\_Et}$) (M8), expressed in the Eyetracker Camera Coordinate Frame (R4); the Gaze Line_Disp ($L_{GazeLine\_Disp}$) (M9), expressed in the Physical Display Coordinate Frame (R3); the Display Gazepoint ($P_{GazePt\_Disp}$) (M10), expressed in the Physical Display Coordinate Frame (R3); and the Gazepoint Pixel ($i_{GazePt\_Pix}$, $j_{GazePt\_Pix}$) (M11), expressed in pixel coordinates (i,j) on the Display Device (H4).

(H6) The Eyetracker Camera is the Eyetracker Device's (H5) (real) video camera that captures Eyetracker Video (M5) of the User's eye activity.

(H7) The Virtual Video Camera is the simulated camera that generates the 2D Video Image (Q[i,j]) (M4) of the GOPD's Virtual 3D Object ($S_{Obj\_Obj}$) (M1). As the Virtual Video Camera moves around within the Virtual Object Coordinate Frame (R1), it may be thought of as riding on a Virtual Video Camera Platform (H7.1).

(H8) A human Observer other than the User (H1) (for example a nurse or doctor interacting with a patient using the PainPoint GOPD system) who may have manual control inputs to the GOPD system.

(H9) An Operator may be either the User (H1) or Observer (H8)

While, technically, a Virtual Video Camera (H7) is neither human nor hardware, this specification includes it among the 'Hx' elements for the convenience of conceptualizing it as real device even though it is not. The virtual and mathematical properties of the Virtual Video Camera (H7) are expressed as mathematical elements 'Mx'.

GOPD Control Loops

As discussed above, GOPD systems contain the following two key control loops:

(L1) The Outer Eye Control Loop takes as its input setpoint the User's Designated Object Point ($P_{DesigPt\_Obj}$) (M13), which is typically derived from the User's Object Gazepoint ($P_{GazePt\_Obj}$) (M12) but may also be set manually by an Operator (H9) via mouse click. Based on the User's Designated Object Point ($P_{DesigPt\_Obj}$) (M13), the Outer Eye Control Loop (L1) sets the setpoint Target Camera State ($C_{TargCam\_Obj}$) (M16) for the Inner Camera Trajectory Control Loop (L2) and, as the Inner Camera Trajectory Control Loop (L2) moves the Virtual Video Camera (H7), the Outer Eye Control Loop (L1) finally updates the 2D Video Image display (Q[i,j]) (M4) in accordance with the current (actual) Camera State ($C_{ActCam\_Obj}$) (M17). See FIG. 4.

(L2) The Inner Camera Trajectory Control Loop, illustrated in FIG. 7, takes as its input setpoint the Target Camera State ($C_{TargCam\_Obj}$) (M16) and guides the trajectory of the Virtual Video Camera (H7) to move from its current (actual) Camera State ($C_{ActCam\_Obj}$) (M17) toward the current Target Camera State ($C_{TargCam\_Obj}$) (M16). The dynamics of the Virtual Video Camera motion (H7) enables the User's Eye/Brain smooth-visual-pursuit capability to visually follow/track the path of the Designated Object Point ($P_{DesigPt\_Obj}$) (M13) on the Virtual Video Camera's (H7) 2D Video Image display (Q[i,j]) (M4) of the Virtual 3D Object ($S_{Obj\_Obj}$) (M1).

GOPD Coordinate Frames

As illustrated in FIG. 3, there are several spatial coordinate frames of reference that are relevant to accurate GOPD operation:

(R1) The Virtual-Object Coordinate Frame is the basic 3D spatial coordinate frame, expressed in spatial distance units, e.g. millimeters, in which the shape of the Virtual 3D Object ($S_{Obj\_Obj}$) (M1) is defined.

(R2) The Virtual-Camera Coordinate Frame represents the perspective of the Virtual Video Camera's (H7) view of is the Virtual 3D Object ($S_{Obj\_Obj}$) (M1). The 2D Image Generator function (F1) uses the Virtual-Camera Coordinate Frame (R2) to generate the 2D Video Image (Q[i, j]) (M4) displayed on the GOPD Display Device (H4).

(R3) The Physical Display Coordinate Frame is the 3D spatial coordinate frame, expressed in spatial distance units, e.g. millimeters, in which both: the millimeter positions ($P_{PixPosn\_Disp}$)[i, j] (M2) of the pixels on the Display Device (H4), and the millimeter coordinate of the User's Display Gazepoint ($P_{GazePt\_Disp}$) (M10) on the Display Device (H4) are defined. The commonality of expressing the User's gazepoint in the same Physical Display Coordinate Frame (R3) as the pixel grid enables the Eyetracker to compute the pixel the User is looking at, Gazepoint Pixel ($i_{GazePt\_Pix}$, $j_{GazePt\_Pix}$) (M11). If the Display Device (H4) is flat, one of the pixel values ($x_{PixPosn\_Disp}$, $y_{PixPosn\_Disp}$, $z_{PixPosn\_Disp}$) is typically set to 0, so, for example, the pixel [i, j] might have the spatial location ($x_{PixPosn\_Disp}$, $y_{PixPosn\_Disp}$, $z_{PixPosn\_Disp}$=0).

(R4) The Eyetracker Camera Coordinate Frame is the spatial 3D coordinate frame, expressed in spatial distance units, e.g. millimeters, that represents the positions of objects and directions of vectors with respect to the physical Eyetracker Camera (H6).

(R5) The Pixel Coordinate Frame, expressed in units of pixels, is the 2D coordinate frame within the Display Device (H4) on which the 2D Video Image (Q[i, j]) (M4) is displayed. The 2 axes of the Pixel Coordinate Frame (R5) are designated by the integers [i,j], enabling a 2D Video Image (Q[i,j]) (M4) to be stored in computer memory as an array.

Key GOPD Mathematical Variables

Key mathematical variables in a preferred GOPD embodiment include:

(Notes: Points in various spatial coordinate frames are expressed as follows: A 3D spatial point in a given 3D coordinate frame is defined as $P_{Type\_Frame}=(x_{Type\_Frame}, y_{Type\_Frame}, z_{Type\_Frame})$, where: 'P' represents a 3D point; 'x', 'y' and 'z' are the coordinate values along the frame's 3 respective axes; the subscript 'Type' indicates the name of the point type; and the subscript 'Frame' indicates the coordinate frame in which the point P is defined. For example, the name of a point on the surface of the Virtual 3D Object, as expressed in the base 3D Object Frame, is $P_{ObjSurfPt\_Obj}=(x_{ObjSurfPt\_Obj}, y_{ObjSurfPt\_Obj}, z_{ObjSurfPt\_Obj})$.

(M1) The Virtual 3D Object ($S_{Obj\_Obj}$) is the GOPD's model, i.e. mathematical representation, of the surface shape of the virtual object to be displayed. A common method to define a complex 3D surface shape is a triangulated irregular network (TIN), which consists of a grid of connected triangular areas, where the three corners of each triangle represent 3D points on the object surface, and the 3D surface coordinates of points inside any triangle are specified by the plane fit through the three corner points. Preferred GOPD embodiments implement the Surface Description of the Virtual 3D Object ($S_{Obj\_Obj}$) (M1) as a pair of cross-referenced lists:

(M1.1) a list of the Object-Surface Points, where the data for each point includes:

(M1.1.1) the spatial coordinates of the object-surface point ($P_{ObjSurfPt\_Obj}[k_{ObjSurfPt}]$), expressed in units of millimeters, within the Virtual-Object Coordinate Frame (R1).

(M1.1.2) the index ($k_{ObjSurfPt}$) of the object surface-point list, and (M1.1.3) the indices ($k_{ObjSurTri}$) of all triangles for which the point is a corner, (M1.2) a list of the Object-Surface Triangles, where the data for each triangle includes:

(M1.2.1) the indices $k_{ObjSurfPt}$ of the triangle's 3 corner points, (M1.2.2) equations for the triangle's 3 edge lines,
(M1.2.3) the equation for the triangle's surface plane,
(M1.2.4) the normal vector for the triangle's individual surface plane,
(M1.2.5) display features such as color, texture, reflectance and/or transparency,
(M1.2.6) the index $k_{ObjSurfTri}$ of the triangle,
(M1.3) a set of Camera Target Control Parameters that specify how the camera should be positioned, oriented and zoomed for any triangle $k_{ObjSurfTri}$ where the Designated Object Point ($P_{DesigPt\_Obj}$) (M13) might land on the Virtual 3D Object ($S_{Obj\_Obj}$) (M1):
(M1.3.1) the target Camera Orientation Angle ($\Gamma_{TargCam\_Obj}$) is the GOPD's prescribed target camera viewing angle for Designated Object Points ($P_{DesigPt\_Obj}$) (M13) that occur within this Object-Surface Triangle (M1.2).

Notes on setting a triangle's target Camera Orientation Angle ($\Gamma_{TargCam\_Obj}$) (M1.3.1):

A triangle's target Camera Orientation Angle ($F_{TargCam\_Obj}$) (M1.3.1) need not align with the triangle surface normal vector. To keep the Virtual Video Camera (H7) from swinging around wildly when the User is looking at regions of high surface curvature, the target viewing angle for a triangle may be set as a weighted average of the surface normal vectors of the local neighboring triangles.

In GOPD applications where it is desired to present the view of the Virtual 3D Object ($S_{Obj\_Obj}$) (M1) in as much of an upright orientation as possible, it is useful to constrain the camera roll angle $\Phi_{TargCam\_Obj}$ to 0, thereby keeping the camera upright.

(M1.3.2) the Default Minimum Imaged Object Width ($W_{DfltMinImgWdth\_Obj}$) is the GOPD camera's default value for the smallest target Imaged Object Width ($W_{TargImgWdth\_Obj}$) (M21.2.2), (i.e. largest desired zoom factor) for cases where the camera is pointed at a Designated Object Point ($P_{DesigPt\_Obj}$) (M13) that exists within this triangle.

(M1.3.3) the Default Maximum Imaged Object Width ($W_{DfltMaxImgWdth\_Obj}$) is the GOPD camera's default value for the largest target Imaged Object Width ($W_{TargImgWdth\_Obj}$) (M21.2.2), (i.e. smallest desired zoom factor) for cases where the camera is pointed at a Designated Object Point ($P_{DesigPt\_Obj}$) (M13) that exists within this triangle.

Note: At the beginning of a GOPD session, the current minimum and maximum Imaged Object Widths (listed below) are initialized to the default Imaged Object Widths (for each object triangle).

(M1.3.4) the target Camera Distance ($D_{TargCamDist\_Obj}$) is the GOPD's prescribed distance of the Virtual Video Camera (H7) from the Designated Object Point ($P_{DesigPt\_Obj}$) (M13) for Designated Object Points ($P_{DesigPt\_Obj}$) (M13) that occur within this triangle.

A GOPD system may be designed to accommodate either of two Virtual Video Camera Types: an Infinite-Distance Camera and a Closeup-Capable Camera. With an Infinite-Distance Camera, the Camera Trajectory Control function (F7) is constrained to position the camera anywhere on the surface of an infinite radius sphere centered at the object origin. with a Closeup-Capable Camera, the camera may be positioned anywhere within the full volume of the Virtual-Object Coordinate Frame (R1).

The key advantage of an Infinite-Distance Camera is simpler GOPD code: in particular, the 2D Image Generator function (F1) can generate the 2D Video Image (Q[i,j]) (M4) of the Virtual 3D Object (M1) as a simple linear projection of the 3D object onto the 2D display plane.

The key advantage of a Closeup-Capable Camera is that it generates more realistic 'closeup' views of the Object, providing the 3D imaging effect of a camera viewing a complex 3D object at close range.

The GOPD system designer chooses the camera type desired for the specific application. (A GOPD system must implement a Closeup-Capable Camera if the application employs a real Physical Video Camera viewing a real object/scene in addition to the Virtual Video Camera (H7) viewing the Virtual 3D Object (M1).)

A GOPD's Virtual Video Camera (H7) may be designed with either of two Camera Zoom Types: a Fixed-Zoom Camera or a Variable-Zoom Camera. A Variable-Zoom Camera has a variable Camera FOV Angle ($\alpha_{TargCamFOV}$) (M21.1.3) that is controllable by the Camera Trajectory Control function (F7), and a Fixed-Zoom Camera has a fixed, uncontrolled angular field of view.

If the GOPD system has either an Infinite-Distance Camera, or a Closeup-Capable Camera that is also a Fixed-Zoom Camera, there is no need for the target Camera Distance variable ($D_{TargCamDist\_Obj}$) (M1.3.4) in the Camera Target Control Parameters (M1.3) set. (As discussed later, if the camera has a fixed Camera FOV Angle, the Zoom Control function (F5) is fully constrained to set the target Camera Distance ($D_{TargCamDist\_Obj}$) (M1.3.4) based on the zoom's Imaged Object Width specification alone, leaving no freedom for independent control of the camera distance.

(M1.4) a set of Zoom Limit Control Variables that allow the User (H1) or Observer (H8) to adjust minimum and maximum zoom factors on local regions of the Virtual 3D Object ($S_{Obj\_Obj}$) (M1) online:

(M1.4.1) the Minimum Imaged Object Width Adjustment ($W_{MinImgWdthAdj\_Obj}$) is the current Operator (H9) adjustment to the Default Minimum Imaged Object Width ($W_{DfltMinImgWdth\_Obj}$) (M1.3.2).

(M1.4.2) the Maximum Imaged Object Width Adjustment ($W_{MaxImgWdthAdj\_Obj}$) is the current Operator (H9) adjustment to the Default Minimum Imaged Object Width ($W_{DfltMaxImgWdth\_Obj}$) (M1.3.).

Note: These minimum and maximum Imaged Object Width Adjustments are initialized to 0 at the beginning of a GOPD session and the User (H1) and/or an Observer (H8) may modify them via manual control during the GOPD session.

(M1.4.3) the Current Minimum Imaged Object Width ($W_{CurMinImgWdth\_Obj}$) is the GOPD camera's current value for the smallest target Imaged Object Width ($W_{TargImgWdth\_Obj}$) (M16.2.2), (i.e. largest desired zoom factor) for cases where the camera is pointed at a Designated Object Point ($P_{DesigPt\_Obj}$) (M13) that exists within this triangle.

(M1.4.4) the Current Maximum Imaged Object Width ($W_{CurMaxImgWdth\_Obj}$) is the GOPD camera's default value for the largest target Imaged Object Width ($W_{TargImgWdth\_Obj}$) (M16.2.2), (i.e. smallest desired zoom factor) for cases where the camera is pointed at a Designated Object Points ($P_{DesigPt\_Obj}$) (M13) that exists within this triangle.

Note: The current minimum and maximum Imaged Object Width values (for any object triangle) are equal to the sum of the default plus adjustment values.

Note: The term Virtual 3D Object ($S_{Obj\_Obj}$) (M1) is intended to include full 3D Scenes, which may include multiple individual objects. It may also include objects within other objects, where inner objects might become visible to the User if the Camera Trajectory Control function (F7) is designed to allow driving the Virtual Video Camera (H7) beneath an outer object surface.

(M2) The Pixel Position array ($P_{PixPosn\_Disp}[i,j]$) specifies the millimeter locations of the Display Device (H4) pixels within the 3D Physical Display Coordinate Frame (R3). This Pixel Position array ($P_{PixPosn\_Disp}[i,j]$) (M2) is used in the Display-To-Pixel Transform function (F8.2) which converts back and forth between pixel indices [i,j] and Pixel Positions ($P_{PixPosn\_Disp}[i,j]$)(M2).

(M3) The Home Pixel ($i_{Home}$, $j_{Home}$) is the (generally fixed) pixel coordinate within the Display Window (H4.1) that represents both:
  a. the center of the 2D Video Image (Q[i,j]) (M4), i.e. the center of Virtual Video Camera's (H7) angular field of view, and
  b. the target toward which the GOPD system the display of the User's Designated Object Point ($P_{DesigPt\_Obj}$) (M13) will finally settle.

Note: The fact that the Home Pixel ($i_{Home}$, $j_{Home}$) (M3) is defined to represent both the center of the Virtual Video Camera's (H7) Image and the center of the Display Window (H4.1) provides the spatial coordination between the Inner Camera Trajectory Control Loop (L2) and the Outer Eye Control Loop (L1).

(M4) The 2D Video Image (Q[i,j]) represents the state of the image display presented to the User on the Display Device (H4). The 2D Video Image (Q[i,j]) (M4) in the GOPD memory is an array of 'Q' values, which represent the color and/or brightness values displayed at each pixel. Thus the 2D Video Image (Q[i,j]) (M4) is represented by the data array Q[i,j] (where the square brackets indicate that the variable Q is an array indexed by the pixel indices i and j).

The GOPD's 2D Image Generator function (F1) computes the Q[i,j] array based on the Virtual 3D Object's Surface Description ($S_{Obj\_Obj}$) (M1) and the current (actual) Camera State ($C_{ActCam\_Obj}$) (M17).

Some pixels in a 2D Video Image (Q[i,j]) (M4) may not represent any point on the Virtual 3D Object surface ($S_{Obj\_Obj}$) (M1). To accommodate these cases, each pixel element of the 2D Video Image (Q[i,j]) (M4) contains a flag variable Image Object Valid ($b_{ImgObjValid}[i,j]$) (M4.1) indicating whether or not a valid Object surface point exists at that pixel.

(M5) The Eyetracker Video is the video image stream of the User's eye activity produced by the Eyetracker Camera (H6).

(M6) The User's Eyeball Position_ET ($P_{Eye\_Et}$) is the spatial position of the Eye (H2) within the Eyetracker Camera Coordinate Frame (R4). The Eyeball Position_ET ($P_{Eye\_Et}$) (M6) is measured by the Eyetracker Processor function (F2) (seen in FIG. 6).

(M7) The Gaze Direction Vector_ET ($V_{GazeDir\_Et}$) is the vector direction of the eye's gaze line line within the Eyetracker Camera Coordinate Frame (R4). Gaze Direction Vector_ET ($V_{GazeDir\_Et}$) (M7), typically a unit vector, is measured by the Eyetracker's Eye Image Processor function (F2.1) (seen in FIG. 6).

(M8) The Eye's Gaze Line_ET ($L_{GazeLine\_ET}$) is the spatial line that specifies the eye's central line of vision, as expressed within the Eyetracker Camera Coordinate Frame (R4). The Eyetracker Processor function (F2) computes Gaze Line_ET ($L_{GazeLine\_ET}$) (M8) as a line that originates at the Eyeball Position_ET ($P_{Eye\_Et}$) (M6) and moves along the Gaze Direction Vector_ET ($V_{GazeDir\_Et}$) (M7).

(M9) The Gaze Line_Disp ($L_{GazeLine\_Disp}$) represents the eye's Gaze Line as expressed within the Physical Display Coordinate Frame (R3). The Eyetracker Processor function (F2) computes Gaze Line_Disp ($L_{GazeLine\_Disp}$) (M9) from Gaze Line_ET ($L_{GazeLine\_ET}$) (M8) using the Eyetracker-To-Display Transform (EtToDispTform) (M30)).

(M10) The User's Display Gazepoint ($P_{GazePt\_Disp}$) is the spatial point, expressed within the Physical Display Coordinate Frame (R3) where the eye's Gaze Line_Disp ($L_{GazeLine\_Disp}$) (M9) intercepts the viewing surface of the Display Device (H4). The Eyetracker Processor function (F2) computes Display Gazepoint ($P_{GazePt\_Disp}$) (M10) in its Compute Gaze-Line/Display-Surface Intercept function (F2.3).

(M11) The User's Gazepoint Pixel ($i_{GazePt\_Pix}$, $j_{GazePt\_Pix}$) is the pixel coordinate of the eye's gazepoint on the Display Device (H4), i.e. the pixel where the eye's gaze line intercepts the surface of the Display Device (H4).

(M12) The User's Object Gazepoint ($P_{GazePt\_Obj}$) is the point on the Virtual 3D Object ($S_{Obj\_Obj}$) (M1) that is displayed at the Gazepoint Pixel ($i_{GazePt\_Pix}$, $j_{GazePt\_Pix}$) (M11) on the Display Device (H4).

Note: A 3D virtual Object Gazepoint ($P_{GazePt\_Obj}$) (M12) does not logically exist if the User's gaze line does not intercept a surface on the virtually displayed object. The preferred embodiment of a GOPD system employs a separate flag variable Object Gazepoint Valid ($b_{GazePtValid}$) (M12.1) to designate the existence or nonexistence of an Object Gazepoint ($P_{GazePt\_Obj}$) (M12).

(M13) The User's visually Designated Object Point ($P_{DesigPt\_Obj}$) is the point on the Virtual 3D Object ($S_{Obj\_Obj}$) (M1) that the User designates with his gaze to direct the GOPD system's control of the Virtual Video Camera's (H7) trajectory. As discussed later, the Designated Object Point ($P_{DesigPt\_Obj}$) (M13) is a smoothed value of the Object Gazepoint ($P_{GazePt\_Obj}$) (M12), derived over several preceding Eyetracker (H5) sample points; not just the current sample.

(M14) The Designated-Point Pixel ($i_{DesigPt}$, $i_{DesigPt}$) is the pixel where the Designated Object Point ($P_{DesigPt\_Obj}$) (M13) is currently displayed on the Display Device (H4).

(M15) The Designated Point Smoothing Time Constant ($T_{DesigPtSmooth}$) specifies the GOPD time constant used to smooth the Object Gazepoint ($P_{GazePt\_Obj}$) (M12) when setting the Designated Object Point ($P_{DesigPt\_Obj}$) (M13).

(M16) A Camera State variable ($C_{CamState\_Obj}$) is a GOPD program data type that represents the position, orientation and zoom variables states of a Virtual Video Camera (H7).

A GOPD system uses two specific instances of a Camera State variable: The Actual Camera State ($C_{ActCam\_Obj}$) (M17) which is the current actual state of the Virtual Video Camera (H7), and the Target Camera State ($C_{TargCam\_Obj}$) (M21), the setpoint toward which is the Camera Trajectory Control function (F6) is currently driving the Virtual Video Camera (H7).

A Camera State variable includes two categories of sub-variables. The Independent Camera State includes the variables that a camera control system can set directly on the camera itself, and the Dependent Camera State includes the variables whose values result from the values of the independent, directly-controlled camera variables.

All sub-variables within a Camera State (M16) are expressed within the Virtual-Object Coordinate Frame (R1).

(M16.1) The Independent Camera State Variables include the following three independent, directly-controlled camera variables for manipulating the camera's (i) position, (ii) orientation and (iii) zoom elements.

(M16.1.1) The Camera Position ($P_{..Cam\_Obj}$) specifies the 3D position of the Virtual Video Camera (H7) within the Virtual-Object Coordinate Frame (R1).

(M16.1.2) The Camera Orientation Angle ($\Gamma_{..Cam\_Obj}$) specifies the 3D angular orientation angle of the Virtual Video Camera (H7) within the Virtual-Object Coordinate Frame (R1). The preferred representation for the camera orientation angle ($\Gamma_{DispCmd\_Obj}$) is an Euler angle sequence $\Gamma_{..Cam\_Obj} = (\Psi_{..Cam\_Obj}, \Theta_{..Cam\_Obj}, \Phi_{..Cam\_Obj})$, where the first rotation $\Psi_{..Cam\_Obj}$ (e.g. azimuth or yaw) takes place in the horizontal plane around the object's vertical axis, the second rotation $\Theta_{..Cam\_Obj}$ (e.g. elevation, pitch or forward/back tilt) takes place around the object's rightward axis, and the third rotation $\Phi_{..Cam\_Obj}$ (e.g. roll or side-to-side tilts) takes place around the object's forward axis.

(M16.1.3) The Camera FOV Angle ($\alpha_{..CamFOV}$), is the Virtual Video Camera's (H7)'s "equipment-equivalent" Zoom Control setting for manipulating the camera's angular field of view.

(M16.2) The Dependent Camera State Variables include two working variables to support the Camera Trajectory Control function (F7) as it computes the above three directly-controlled camera variables. From the standpoint of a camera, these 'working' variables are dependent variables whose values result from the values of the directly-controlled camera variables.

(M16.2.1) the Camera-To-Object Distance ($D_{..CamToObjDist}$) is the distance between the Camera Position ($P_{..Cam\_Obj}$) (M16.2.1) and the Designated Object Point ($P_{DesigPt\_Obj}$) (M13).

(M16.2.2) the Imaged Object Width ($W_{..ImgWdth\_Obj}$) is the linear width of the Virtual 3D Object (M1) seen by the Virtual Video Camera's (H7) 2D Video Image (Q[i,j]) (M4). This Imaged Object Width ($W_{..ImgWdth\_Obj}$) (M16.2.2) is controlled by a combination of the Camera-To-Object Distance ($D_{..CamToObjDist}$) (M16.2.1) and the Camera FOV Angle ($\alpha_{..CamFOV}$) (M16.1.3).

Note: The units of the Imaged Object Width are the same distance units used to describe the Virtual 3D Object ($S_{Obj\_Obj}$) (M1) (See FIG. 4.)

Notes on Camera State variables:

The '..' notation in the subscripts of the above variables indicate that the variables may represent either 'Act' for Actual (M17) or 'Targ' for Target (M21) Camera States.

Each of the individual variables in the Independent Camera State Variables, are also designated as $u_k(t_n)$, where: $u_k$ represents $k^{th}$ element of the camera control state set; the subscript k denotes the specific element of the set; and to represents the occurrence time of the GOPD's $n^{th}$ loop iteration.

(M17) The Actual Camera State ($C_{ActCam\_Obj}$) [as opposed to the Target Camera State ($C_{TargCam\_Obj}$) (M21)] represents the current actual state of the Virtual Video Camera (H7) as it moves around during a GOPD run.

(M18) The Gazepoint Variation ($W_{GazPtVar}$) is the magnitude of the variation in the User's recent gazepoint path on the Virtual 3D Object (M1), measured over the recent Zoom Time Constant ($T_{Zoom}$) (M19).

(M19) The Zoom Time Constant ($T_{Zoom}$) is the length of time over which the Zoom Control function (F5) computes the Gazepoint Variation ($W_{GazePtVar}$) (M18) of the User's recent gaze path.

(M20) The Zoom Control Constant ($K_{ZoomCtrl}$) is the unitless constant of proportionality that the Zoom Control function (F5) uses to compute the GOPD's target Imaged Object Width ($W_{TargImgWdth\_Obj}$) (M21.2.2) from the User's recent Gazepoint Variation ($W_{GazePtVar}$) (M18).

(M21) The Target Camera State ($C_{TargCam\_Obj}$) [as opposed to the Actual Camera State ($C_{ActCam\_Obj}$) (M17)] is the GOPD set-point Camera State (including position, orientation and zoom) toward which the GOPD control system drives the Virtual Video Camera (H7) in order to view a given Designated Object Point ($P_{DesigPt\_Obj}$) (M13). Note: When the Actual Camera State ($C_{ActCam\_Obj}$) (M17) reaches the Target Camera State ($C_{TargCam\_Obj}$) (M21), the image of the Designated Object Point ($P_{DesigPt\_Obj}$) (M13) appears at the Display Device's Home Pixel location ($i_{Home}, j_{Home}$) (M3). (See the later description of the Target Camera-State Calculator function (F6).

(M22) The Camera State Error ($C_{CamError\_Obj}$) indicates how far the Target Camera State ($C_{TargCam\_Obj}$) (M21) is from the Actual Camera State ($C_{ActCam\_Obj}$) (M17). Each element of the Camera State Error ($C_{CamError\_Obj}$) (M22) describes how much that particular element variable must change for the Virtual Video Camera (H7) to reach the "target" state where the Virtual Video Camera (H7) produces the ultimately desired target view of the User's currently Designated Object Point ($P_{DesigPt\_Obj}$) (M13).

(M23) The Camera Velocity Control Time Constants ($T_{CamVel}[k]$) (M23) are the time constants that the Camera Trajectory Control function (F7) uses to regulate the Virtual Video Camera (H7) motion as it moves from its Actual Camera State ($C_{ActCam\_Obj}$) (M17) toward its current Target Camera State ($C_{TargCam\_Obj}$) (M21).

(M24) The Camera State Velocity ($V_{ActCam\_Obj}$), computed by the GOPD's Camera Trajectory Control function (F7), represents the current control velocities applied to the various elements of the camera's Actual Camera State ($C_{ActCam\_Obj}$) (M17). The magnitude of the Actual Camera State Velocity ($V_{ActCam\_Obj}$) (M24) is a function of the Actual Camera State Error ($C_{CamError\_Obj}$) (M22) but is limited to a Camera Velocity Limit ($V_{CamLimit\_Obj}$) (M24.1).

(M25) The Control Loop Sample Interval ($\Delta T_{samp}$) is the time between consecutive GOPD iteration samples. This interval is typically, but not necessarily, a GOPD system constant related to the camera frame rate.

(M26) The Camera State Increment ($\Delta C_{CamState\_Obj}$) represents the amount that the GOPD's Camera Trajectory Control function (F7) shifts the Actual Camera State ($C_{ActCam\_Obj}$) (M17) during the current GOPD iteration. The amount is generally a portion of the Camera State Error ($C_{CamError\_Obj}$) (M22), limited so the User's Eyes can easily follow the motion of his Designated Object Point ($P_{DesigPt\_Obj}$) (M13) as the Camera Trajectory Control function (F7) shifts the display of that point.

(M27) The Object Home Point ($P_{HomePt\_Obj}$) is the point on the Virtual 3D Object (M1), if any, that is currently displayed at the Home Pixel ($i_{Home}, j_{Home}$) (M3) of the Display Device (H4). An Object Home Point Flag ($b_{ObjHomePtExist}$) (M27.1), indicating whether or not an object point exists at the Home Pixel ($i_{Home}, j_{Home}$) (M3), accompanies the Object Home Point ($P_{HomePt\_Obj}$) (M27).

(M28) The Virtual-Object-To-Camera Coordinate Transform (VirtObjToCamTform) defines the mathematical transform allowing points and vectors to be converted back and forth between the 3D Virtual-Object Coordinate Frame (R1) and the 3D Virtual-Camera Coordinate Frame (R2).

(M29) The Object-To-Disp Coordinate Transform (ObjToDispTform) defines the mathematical transform allowing points and vectors to be converted back and forth between the 3D Virtual-Object Coordinate Frame (R1) and the 3D Physical Display Coordinate Frame (R3).

(M30) The Eyetracker-To-Display Coordinate Transform (EtToDispTform) defines the mathematical transformation allowing points and vectors to be converted between the 3D Eyetracker Camera Coordinate Frame (R4) and the 3D Physical Display Coordinate Frame (R3).

Notes on Mathematical Variables:

The above discussion of the GOPD's mathematical variables addresses the use of only a single eye, as if the Eyetracker Device (H5) were tracking only one eye. Though GOPD is capable of operating with a single eye, binocular eyetrackers may be used to advantage to obtain better a measurement of the User's gazepoint by averaging the measurements from both eyes.

The variables in the above list are stored in computer memory, and their values, which vary as a function of time, represent the current state of the GOPD processing.

All coordinate transformations include both forward and inverse processes, allowing points, lines and vectors to be converted from either frame to the other. The mathematics of coordinate frame transformations are well known and are not discussed here.

With minor extensions to the mathematics described here, the GOPD concept can be implemented with stereoscopic or 3D displays as well as 2D displays.

In the example PainPoint GOPD application discussed earlier, the Virtual-Object Coordinate Frame (R1) for a virtual human body might be defined to have:

a) an origin at the center of the stomach,
b) an x axis pointing out the right side of the body,
c) a y axis pointing out the front of the body, and
d) a z axis pointing out the top of the body.

The origin of the Virtual-Object Coordinate Frame (R1), defined to be the center of the stomach, would be represented by the coordinate $x_o=0$, $y_o=0$, $z_o=0$.

GOPD Design and Operation

A block diagram of a preferred embodiment of a GOPD system is shown in FIG. 5. FIGS. 6 and 7 show more detailed sub diagrams.

GOPD's Iterative Operation

In various embodiments, the GOPD system executes its dynamic, real-time control operations by iteratively cycling through the Outer Eye Control Loop (L1) functions shown in FIG. 5. The iterative loop is executed at the Control Loop Sample Interval ($\Delta T_{samp}$) (M25). Ideally, the GOPD equipment operates at a sample rate of 30 Hz or higher, allowing the human eye to perceive the motion of the displayed object motion as smooth.

At each iteration, the system executes a single pass through all the outer loop functions shown in FIG. 5. Detailed descriptions of the GOPD's high-level functions follow:

GOPD User Operations

During GOPD operation: the User's Eyes (H2) see the displayed image, the User's Brain (H3) processes the image, the User's Brain (H3) identifies a point of interest on the object displayed on the image, and the User's Brain (H3) directs the eyes to either visually track/follow the current point of interest on the displayed object or saccade to an alternative point of interest.

Each GOPD iteration begins with the Eyetracker Device (H5) sampling the state of the User's gaze as he observes the 2D Video Image (Q[i,j]) (M4) that the GOPD equipment generated and displayed in the prior iteration.

Eyetracker Processor Function (F2)

The Eyetracker's (H5) Eyetracker Camera (H6) observes the User's Eye or eyes (H2) and passes the Eyetracker Video (M5) to the Eyetracker Processor function (F2) which measures the Gazepoint Pixel coordinate ($i_{GazePt\_Pix}$, $j_{GazePt\_Pix}$) (M11) on the Display Device (H4). (See more Eyetracker (H5) details in FIG. 6.)

In preferred embodiments of GOPD systems, the Eyetracker Camera (H6) is mounted in a known or measurable position and orientation with respect to the 2D Display Device (H4). To obtain an optimum view of the User's Eyes (H2), i.e. the eyeballs themselves, the Eyetracker Camera (H6) is typically mounted below the Display Device (H4).

As shown in FIG. 6, the Eyetracker Processor function (F2) executes the following steps:

Given the inputs:
 a. the Eyetracker Camera's (H6) Eyetracker Video (M5) of the User's Eye(s) (H2) and
 b. the Eyetracker Camera's (H6) known location and orientation with respect to the GOPD's 2D Display Device (H4), the Eye Image Processor (F2.1) computes:
 a. the 3D Eyeball Position_ET ($P_{Eye\_Et}$) (M6), i.e. the spatial coordinate of the eyeball, and
 b. 3D Gaze Direction Vector_ET ($V_{GazeDir\_Et}$) (M7), i.e. the spatial direction of the Eye's (H2) pointing direction, within the Eyetracker Camera Coordinate Frame (R4).

The Gaze Line Calculator function (F2.2) computes the eye's 3D Gaze Line_ET (M8), i.e. the eye's line of sight that originates at the Eyeball Position_ET ($P_{Eye\_Et}$) (M6) and proceeds indefinitely along the eye's Gaze Vector Direction ET ($V_{GazeDir\_Et}$) (M7). Recall: Gaze Line_ET is the gaze line expressed in the Eyetracker Camera Coordinate Frame (R4).

The GOPD's 3D Coordinate Frame Transformation function (F8.1) uses the Eyetracker-To-Display Transform (EtToDispTform) (M30) to transform Gaze Line_ET ($L_{GazeLine\_ET}$) (M8), expressed in the Eyetracker Camera Coordinate Frame (R4) to the Gaze Line_Disp ($L_{GazeLine\_Disp}$) (M9), expressed within the Physical Display Coordinate Frame (R3).

The Compute Gaze-Line/Display-Surface Intercept function (F2.3). computes the 2D Display Gazepoint ($P_{GazePt\_Disp}$) (M10), i.e. the spatial coordinate ($x_{Gaze\_Disp}$, $y_{Gaze\_Disp}$) on the Display Device (H4) surface where the User is currently looking. The gazepoint is computed mathematically as the point where the Gaze Line_Disp ($L_{GazeLine\_Disp}$) (M9) intercepts the Display Device (H4) surface. (The z component $z_{Gaze\_Disp}$ of the gazepoint on the 2D display surface is assumed to be 0.)

The GOPD's Display-to-Pixel Transform function (F8.2) transforms the spatial Display Gazepoint ($P_{GazePt\_Disp}$) (M10) to the User's Gazepoint Pixel ($i_{GazePt\_Pix}$, $j_{GazePt\_Pix}$) (M11) i.e. the pixel coordinate corresponding to the eye's gazepoint on the Display Device (H4).

Further details on preferred embodiments of the Gaze Line Calculator function (F2.2) discussed in the above steps, are provided in U.S. Pat. Nos. 7,686,451 and 7,997,730, by Cleveland, D. et al. botb named Explicit Raytracing for Gimbal-Based Gazepoint Trackers, whose contents are included here in their entirety. For purposes of this current GOPD specification, essential Eyetracker Device (H5) features discussed in these referenced patents include:

While many eyetrackers use fixed cameras, whose positions are fixed with respect to the display or scene the user is observing, more advanced eyetrackers may use motorized, gimbal-based cameras. Gimbal based eyetracking cameras:

a. keep the camera pointed at and focused on the eye as the user moves his head around, allowing the user large freedom of head movement within the available camera field of view, and b. support the use of telephoto lenses that provide high resolution images of the eye, allowing high accuracy eyetracking despite large head movements.

While many eyetrackers use simplified lumped-parameter algebraic models to compute the user's gazepoint from the PCCR's pupil-center and corneal-reflection location data in the eye image, gimbal-based eyetrackers require the use of physically explicit mathematical models to accurately calculate the individual physical effects of:

a. the camera motion, including its varying position, orientation and focus condition with respect to both the eye and the display/scene, and b. the anatomical structure of the individual eye being tracked (including the eye's angle Kappa describing the offset between the eye's optic and visual axes, and the shape of the corneal surface describing how the location of the corneal surface shifts with respect to pupil location as a function of the eye's spatial orientation angle).

Object Point Lookup Function (F3)

While an eyetracker device is typically able to measure the spatial and/or pixel coordinates of a gazepoint on a display device, the eyetracker does not know what within the image itself is being displayed at that coordinate. More specifically, the eyetracker itself does not associate the measured gazepoint coordinate on the Display Device with the contextual or semantic significance of the image at that point.

In GOPD systems, which drive the Virtual Video Camera (H7) based on the User's Gazepoint on the image of the Virtual 3D Object surface ($S_{Obj\_Obj}$) (M1), the key semantic significance of the Gazepoint Pixel ($i_{GazePt\_Pix}$, $j_{GazePt\_Pix}$) (M11) is the 3D position on the Virtual 3D Object ($S_{Obj\_Obj}$) (M1) that is displayed at the Gazepoint. The purpose of the GOPD's Object Point Lookup function (F3) is to associate the User's Gazepoint Pixel ($i_{GazePt\_Pix}$, $j_{GazePt\_Pix}$) (M11) with the corresponding the Object Gazepoint ($P_{GazePt\_Obj}$) (M12) displayed at that point.

The GOPD's Object Point Lookup function (F3) computes this semantic connection as follows. It:

a. Takes as its input the User's Gazepoint Pixel ($i_{GazePt\_Pix}$, $j_{GazePt\_Pix}$) (M11)—as computed earlier by the Eyetracker Processor Function (F2), b. Computes the pixel's line-of-sight in the Virtual-Camera Coordinate Frame (R2), where the pixel line-of-sight is the straight, unrefracted line that passes through the center of the camera lens to the pixel location on camera sensor.

c, Converts the pixel line-of-sight from the Virtual-Camera Coordinate Frame (R2) to the Virtual-Object Coordinate Frame (R1), d. Projects the pixel line-of-sight, as expressed in the Virtual-Object Coordinate Frame (R1), back out from the pixel through the camera lens center to the first point (if any) where it intercepts the virtual object surface, and e, Returns the Object Gazepoint ($P_{GazePt\_Obj}$) (M12), which is the point on the Virtual 3D Object ($S_{Obj\_Obj}$) (M1) that is displayed at the User's Gazepoint Pixel ($i_{GazePt\_Pix}$, $j_{GazePt\_Pix}$) (M11) on the Display Device (H4).

Note, the above steps b), c) and d), which compute the underlying pixel line-of-sight geometry and find the line/object intercept, are identical to these steps done in the GetPixelColor function (F1.1), discussed later in the 2D Image Generator Function (F1) section. The key difference between the two functions is that this Object Point Lookup Function (F3) returns the object spatial position corresponding to the argument pixel [i,j] while the GetPixelColor function (F1.1) returns the display color of the argument pixel [i,j].

If the User looks at a point on the display where no part of the Virtual 3D Object ($S_{Obj\_Obj}$) (M1) exists, the Object Gazepoint Valid flag ($b_{GazePtValid}$) (M12.1) is also declared invalid.

Designated Object Point Calculator Function (F4)

The purpose of the Designated Object Point Calculator Function (F4) is to determine the Designated Object Point ($P_{DesigPt\_Obj}$) (M13) based on the recent history of the User's Object Gazepoint ($P_{GazePt\_Obj}$) (M12) on the displayed image of the Virtual 3D Object ($S_{Obj\_Obj}$) (M1).

In an overly simple GOPD embodiment, the Designated Object Point ($P_{DesigPt\_Obj}$) (M13) could be set directly equal to the single sample of the User's currently computed Object Gazepoint ($P_{GazePt\_Obj}$) (M12). In practice, however, the Object Gazepoint ($P_{GazePt\_Obj}$) (M12) signal can produce significant sample-to-sample noise. Thus, in preferred GOPD embodiments, the Designated Object Point Calculator function (F4):

a. maintains a recent history of the measured Object Gazepoint ($P_{GazePt\_Obj}$) (M12) sample values, and b. computes the Designated Object Point ($P_{DesigPt\_Obj}$) (M13) as a smoothed value of that history, where the best value of the Designated Point Smoothing Time Constant ($T_{DesigPtSmooth}$) (M15) depends on the GOPS application which is typically three to five gaze fixation periods.

There are two key sources of noise in the GOPD system's measurement of the User's Object Gazepoint ($P_{GazePt\_Obj}$) (M12):

a. The Eyetracker instrument (H5) produces noise in its measurement of the Gazepoint Pixel ($i_{GazePt\_Pix}$, $j_{GazePt\_Pix}$) (M11). Camera image noise, eye image processing noise, and eye calibration errors each contribute to an eyetracker's overall gazepoint-measurement noise.

b. The Object Point Lookup function (F3) can strongly amplify eyetracking errors when the Gazepoint Pixel ($i_{GazePt\_Pix}$, $j_{GazePt\_Pix}$) (M11) occurs at an object-surface point that is currently displayed at an oblique angle with respect to the User's view of the object. In these instances, small variations in the Gazepoint Pixel ($i_{GazePt\_Pix}$, $j_{GazePt\_Pix}$) (M11) result in large variations along the Virtual 3D Object surface ($S_{Obj\_Obj}$) (M1), in turn producing jittery overall GOPD operation.

One method for the Designated Object Point Calculator function (F4) to minimize noise in the Designated Object Point ($P_{DesigPt\_Obj}$) (M13) is to:

a. reduce relative smoothing weights on Object Gazepoint samples ($P_{GazePt\_Obj}$) (M12) whose object normal vector varies significantly from the viewing vector, and b. place no smoothing weight on invalid Object Gazepoint samples ($P_{GazePt\_Obj}$) (M12), where no part of the Virtual 3D Object surface ($S_{Obj\_Obj}$) (M1) is displayed at the Gazepoint Pixel ($i_{GazePt\_Pix}$, $j_{GazePt\_Pix}$) (M11).

Zoom Control Function (F5)

The purpose of the Zoom Control function (F5) is to zoom the displayed image of the Virtual 3D Object ($S_{Obj\_Obj}$) (M1) in and out appropriately as the User operates the system, typically zooming in when the User concentrates his gaze on smaller areas within the Virtual 3D Object ($S_{Obj\_Obj}$) (M1), and zooming out as he spreads his gaze over larger areas.

Because the general term 'Zoom Factor' is vague, GOPD systems more precisely express zoom in terms of the linear width of the portion of Virtual 3D Object ($S_{Obj\_Obj}$) (M1) that is displayed to the User. The GOPD variable used to express zoom is the Imaged Object Width ($W_{TargImgWdth\_Obj}$) (M21.2.2). Note that Zoom Factor and Imaged Object Width ($W_{TargImgWdth\_Obj}$) (M21.2.2) are inversely related: smaller view widths indicate higher, narrower Zoom Factors, and conversely larger view widths indicate lower, wider Zoom Factors.

At the beginning of a GOPD session, the system generally has no knowledge of what the User wants to look at, so it is typically logical to initialize the Designated Object Point ($P_{DesigPt\_Obj}$) (M13) at a central point on the Virtual 3D Object ($S_{Obj\_Obj}$) (M1) and to initialize the target Imaged Object Width ($W_{TargImgWdth\_Obj}$) (M21.2.2) to provide a full field of view that includes the whole Virtual 3D Object ($S_{Obj\_Obj}$) (M1).

In a preferred GOPD embodiment of the Zoom Control Function (F5), the target Imaged Object Width ($W_{TargImgWdth\_Obj}$) (M21.2.2) is controlled to be proportional to the magnitude of the User's recent Gazepoint Variation (w GazPtVar) (M18) on the displayed object. Thus, as the User's gazepoint concentrates on smaller object areas, the GOPD system zooms in; and when the range of the recent object gazepoint pattern expands, the GOPD system zooms out.

Note that both the target Imaged Object Width ($W_{TargImgWdth\_Obj}$) (M21.2.2) and the Gazepoint Variation ($W_{GazPtVar}$) (M18) are expressed in units of linear distance within the Virtual-Object Coordinate Frame (R1). Thus, one method for controlling GOPD zoom is to set the target Imaged Object Width ($W_{TargImgWdth\_Obj}$) (M21.2.2) proportional to the magnitude of the User's recent Gazepoint Variation ($W_{GazPtVar}$) (M18):

$$W_{TargImgWdth\_Obj} = K_{ZoomCtrl} * W_{GazePtVar} \quad \text{(Eqn 1)}$$

where:

$W_{TargImgWdth\_Obj}$ (M21.2.2) is the width of the GOPD's target Imaged Object Width, i.e. the linear width of the Virtual 3D Object ($S_{Obj\_Obj}$) (M1) captured in Virtual Video Camera's (H7) 2D Video Image (Q[i,j]) (M4).

$W_{GazPtVar}$ (M18) is the magnitude of the User's Gazepoint Variation (W GazPtVar) (M18), evaluated on the Virtual 3D Object ($S_{Obj\_Obj}$) (M1) over the recent Zoom Time Constant ($T_{Zoom}$) (M19)).

$T_{Zoom}$ (M19) is the Zoom Time Constant, i.e. the length of time over which the Zoom Control function (F5) computes the Gazepoint Variation ($W_{GazPtVar}$) (M18) of the User's recent gaze path.

$K_{ZoomCtrl}$ (M20) is the Zoom Control Constant of proportionality between the User's recent Gazepoint Variation (w GazPtVar) (M18) and the target Imaged Object Width ($W_{TargImgWdth\_Obj}$) (M21.2.2).

Note that the Zoom Control Constant ($K_{ZoomCtrl}$) (M20) is unitless.

One method for measuring the magnitude of the Gazepoint Variation (W GazPtVar) (M18) over the recent Zoom Time Constant ($T_{Zoom}$.) (M19) is to compute the standard deviation of the gazepoint's path over the Virtual 3D Object ($S_{Obj\_Obj}$) (M1) during that period. As is well known in mathematics, computing the standard deviation of a curve involves first finding the curve average, or mean, value of all the original sample points, then computing the curve variance as the mean of the squares of the differences between each sample and the curve mean, and finally setting the curve standard deviation to the square root of the curve variance. (Sometimes, using variable weights on past time samples within the $T_{Zoom}$ period, e.g. weighting more recent samples more heavily, is useful to balance speed and smoothing in GOPD operation.)

In GOPD Zoom Control it is generally useful to set minimum and maximum values for the target Imaged Object Width ($W_{TargImgWdth\_Obj}$) (M21.2.2). To accommodate both the general purpose of a GOPD application and the detailed nature of different regions on the specific object, a preferred GOPD embodiment allows the system designer to specify the minimum and maximum Imaged Object Widths as a function of the point on the Virtual 3D Object ($S_{Obj\_Obj}$) (M1) that the Virtual Video Camera (H7) is pointed at. The Default Minimum Imaged Object Width ($W_{DfltMinImgWdth\_obj}$) (M1.3.2) and the Default Maximum Imaged Object Width ($W_{DfltMaxImgWdth\_Obj}$) (M1.3.3) are defined for each Object-Surface Triangle (M1.2) in the Virtual 3D Object model ($S_{Obj\_Obj}$) (M1).

Because there is typically no reason to display an area significantly greater than the full size of the Virtual 3D Object ($S_{Obj\_Obj}$) (M1) itself, the Default Maximum Imaged Object Width ($W_{MaxImgWdth\_Obj}$) (M1.3.3) is typically set to the maximum dimension of the object when viewed from the desired Camera Orientation Angle ($\Gamma_{TargCam\_Obj}$) (M1.2.7). On the other hand, the Default Minimum Imaged Object Width ($W_{MinImgWdth\_Obj}$) (M1.3.3) is often set as a function of the application-specific significance of the point or region on the Virtual 3D Object ($S_{Obj\_Obj}$) (M1). Generally, the minimum width should be large enough to display useful object details available within the object model. For example, the minimum display width should generally include a sufficient number of model surface triangles for the user to be able to recognize the object region from the current display.

Target Camera-State Calculator Function (F6)

The general purpose of the Target Camera-State Calculator function (F6) in GOPD applications is to compute the Target Camera State ($C_{TargCam\_Obj}$) (M21) required to provide a desired optimal camera view for any given Designated Object Point ($P_{DesigPt\_Obj}$) (M13) on the Virtual 3D Object ($S_{Obj\_Obj}$) (M1). See FIG. 5. Recall that the Target Camera State ($C_{TargCam\_Obj}$) (M21) is the setpoint for the following Camera Trajectory Control function (F7), and that the Actual Camera State ($C_{ActCam\_Obj}$) (M17) takes some time to catch up to the Target Camera State ($C_{TargCam\_Obj}$) (M21) as the GOPD session progresses.

Recall that the parameters for computing a Target Camera State (M21) for points on the object are contained in the Camera Target Control Parameters (M1.3), which in this GOPD embodiment are part of the Virtual 3D Object model (M1). A set of Camera Target Control Parameters (M1.3) exist for each triangle $k_{ObjSurfTri}$ on the object surface, so the Target Camera-State Calculator Function (F6) can compute a Target Camera State (M21) at any point on the of the Virtual 3D Object model (M1).

The conditions for a Target Camera State ($C_{TargCam\_Obj}$) (M21) to provide an optimal camera view of any given Designated Object Point ($P_{DesigPt\_Obj}$) (M13) are defined by the following properties of the 2D Video Image (Q[i,j]) (M4) that the Virtual Video Camera (H7) produces:

a. The image of the Designated Object Point ($P_{DesigPt\_Obj}$) (M13) appears at the Display Device's (H4) Home Pixel ($i_{Home}$, $j_{Home}$) (M3).

b. The image's perspective angular view replicates the desired Camera Orientation Angle ($\Gamma_{TargCam\_Obj}$) (M1.3.1) specified in the Virtual 3D Object ($S_{Obj\_Obj}$) (M1).

c. The camera's current Imaged Object Width ($W_{CurImgWdth\_Obj}$) (M17.2.2) matches the target Imaged Object Width ($W_{TargImgWdth\_Obj}$) (M21.2.2) computed by the Zoom Control Function (F5).

As discussed earlier, a GOPD system may be designed with either a Fixed-Zoom Camera or a Variable-Zoom Camera. As is well known in the field of photography, the zoom factor of an image can be controlled by changing the distance of the camera from the object, or, if the camera is equipped with a variable zoom capability, by setting the distance independently and then setting the angular field of view as necessary to match the desired image width on the object. The same concept applies for GOPD cameras. The following discussion presents different Target Camera-State Calculator function (F6) procedures for Fixed-Zoom Cameras and Variable-Zoom Cameras.

As illustrated in FIG. 4, the geometric relationship between the camera's angular field-of-view setting α (whether fixed or variable), the camera's spatial field of view W, and the distance D of the object from camera is:

$$\tan(\alpha/2) = W/2D \quad \text{(Eqn 2a)}$$

where:

α is the target Camera FOV Angle ($\alpha_{TargCamFOV}$) (M21.3), i.e. the Virtual Video Camera's (H7) "hardware-equivalent" zoom control setting for manipulating the camera's angular field of view.

W is the target Imaged Object Width ($V_{TargImgWdth\_Obj}$) (M21.2.2), i.e. the linear length, measured along the Virtual 3D Object, seen across the width of the camera image, and D is the target Camera-To-Object Distance ($D_{TargCamToObjDist}$) (M21.2.1), i.e. the distance of the Virtual Video Camera (H7) from the Designated Object Point ($P_{DesigPt\_Obj}$) (M13) on the surface of the Virtual 3D Object ($S_{Obj\_Obj}$) (M1).

If the GOPD system has a Fixed-Zoom Camera, the angular FOV a is a constant, and the GOPD's effective display zoom W is controlled by adjusting the distance D of the camera from the Designated Object Point ($P_{DesigPt\_Obj}$) (M13). The process to compute the Target Camera State ($C_{TargCam\_Obj}$) (M21) is:

a. Set the target Camera FOV Angle ($\alpha = \alpha_{TargCamFOV}$) (M21.3) to the camera's fixed FOV angle α.

b. Find the index $k_{ObjSurfTri}$ of the Object-Surface Triangle (M1.2) on the Virtual 3D Object model ($S_{Obj\_Obj}$) (M1) that contains the current Designated Object Point ($P_{DesigPt\_Obj}$) (M13).

c. Set the target Camera Orientation Angle ($\Gamma_{TargCam\_Obj}$) (M21.2) from the $k_{ObjSurfTri}$th Object-Surface Triangle's Camera Orientation Angle ($F_{TargCam\_Obj}$) (M1.3.1) prescribed in the Virtual 3D Object model ($S_{Obj\_Obj}$) (M1).

d. Set the target Imaged Object Width ($W = W_{TargImgWdth\_Obj}$) (M21.2.2) equal to the currently desired Imaged Object Width ($W_{TargImgWdth\_Obj}$) (M12.2.2), which was previously set by the Zoom Control function (F5).

e. Use the following form of Equation 2a to set the target Camera-To-Object Distance ($D = D_{TargCamToObjDist}$) (M21.2.1) required for the camera image to see the target Imaged Object Width ($W = W_{TargImgWdth\_Obj}$) (M21.2.2), given the target Camera FOV Angle ($\alpha = \alpha_{TargCamFOV}$) (M21.3):

$$D = W/(2 \tan(\alpha/2)) \quad \text{(Eqn 2b)}$$

f. Formulate a target Camera Sight Line ($L_{SightLine}$) that originates at the User's Designated Object Point ($P_{DesigPt\_Obj}$) (M13) and moves in the opposite direction of the target Camera Orientation Angle ($\Gamma_{TargCam\_Obj}$) (M21.2).

g. Set the target Camera Position ($P_{TargCam\_Obj}$) (M21.1) to be the point on Camera Sight Line ($L_{SightLine}$) where the camera is the Camera-To-Object Distance ($D = D_{TargCamToObjDist}$) (M21.2.1) from the Designated Object Point ($P_{DesigPt\_Obj}$) (M13).

On the other hand, if the GOPD system has a Variable-Zoom Camera, a is a variable, and the process to compute the Target Camera State ($C_{TargCam\_Obj}$) (M21) is:

a. Find the index $k_{ObjSurfTri}$ of the Object-Surface Triangle (M1.2) on the Virtual 3D Object model ($S_{Obj\_Obj}$) (M1) that contains the current Designated Object Point ($P_{DesigPt\_Obj}$) (M13).

b. Set the target Camera Orientation Angle ($\Gamma_{TargCam\_Obj}$) (M21.1.2) from the $k_{ObjSurfTri}$th Object-Surface Triangle's Camera Orientation Angle ($\Gamma_{TargCam\_Obj}$) (M1.3.1) prescribed in the Virtual 3D Object model ($S_{Obj\_Obj}$) (M1), c. Set the target Imaged Object Width ($W = W_{TargImgWdth\_Obj}$) (M21.2.2) equal to the currently desired Imaged Object Width $W_{TargImgWdth\_Obj}$ (M21.2.2), which was previously set by the Zoom Control function (F5).

d. Set the target Camera-To-Object Distance ($D = D_{TargCamToObjDist}$) (M21.2.1) from the $k_{ObjSurfTri}$th Object-Surface Triangle's target Camera Distance ($D_{TargCamDist\_Obj}$) (M1.3.4) specified in the Virtual 3D Object model ($S_{Obj\_Obj}$) (M1).

e. Formulate a target Camera Sight Line ($L_{SightLine}$) that originates at the User's Designated Object Point ($P_{DesigPt\_Obj}$) (M13) and moves in the opposite direction of the target Camera Orientation Angle ($\Gamma_{TargCam\_Obj}$) (M21.2), f. Set the target Camera Position ($P_{TargCam\_Obj}$) (M21.1) to be the point on Camera Sight Line ($L_{SightLine}$) where the camera is the Camera-To-Object Distance ($D = D_{TargCamToObjDist}$) from the Designated Object Point ($P_{DesigPt\_Obj}$) (M13), and g. Use the following form of Equation 2a to compute the target Camera FOV Angle ($\alpha = \alpha_{TargCamFOV}$) (M21.3) from the target Imaged Object Width ($W = W_{TargImgWdth\_Obj}$) (M21.2.2) and the target Camera-To-Object Distance ($D = D_{TargCamToObjDist}$) (M21.2.1):

$$\alpha = 2 \tan^{-1}(W/2D) \quad \text{(Eqn 2c)}$$

Toward the GOPD objective of driving the Virtual Video Camera (H7) and its corresponding display of the Virtual 3D Object ($S_{Obj\_Obj}$) (M1) to follow the User's current Designated Object Point ($P_{DesigPt\_Obj}$) (M13), the GOPD System updates the Target Camera State ($C_{TargCam\_Obj}$) (M21) each GOPD iteration.

Note: In the above description for computing a Target Camera State ($C_{TargCam\_Obj}$) (M21), the state is constant for a point anywhere within a given surface triangle. If the Designated Object Point ($P_{DesigPt\_Obj}$) (M13), however, happens to transition incrementally back and forth between two adjacent triangles with significantly different Camera Orientation Angle ($F_{TargCam\_Obj}$) (M21.1.2), the GOPD performance may become unsteady as the designated point jumps back and forth between the two triangles. To minimize such unsteady operation:

additional triangles may be added to the Virtual 3D Object surface model ($S_{Obj\_Obj}$) (M1), or the Target Camera-State Calculator function (F6) may be modified to compute a Target Camera State ($C_{TargCam\_Obj}$) (M21) based on a weighted average of adjacent triangles, where the relative weight on each triangle increases as a function of the closeness of the Designated Object Point ($P_{DesigPt\_Obj}$) (M13) to the center of the triangle.

Camera Trajectory Control Function (F7)

A key feature of GOPD system operation is that the Camera Trajectory Control Function (F7) substantially eliminates the need for head and body motion as the User looks around at a 3D object.

Given the current value of the Target Camera State ($C_{TargCam\_Obj}$) (M21) computed by the Target Camera-State Calculator function (F6), the high-level purpose of the Camera Trajectory Control function (F7) is to manage the dynamic motion of the Virtual Video Camera (H7) trajectory around the Virtual 3D Object ($S_{Obj\_Obj}$) (M1) to produce a 2D Video Image display (Q[i,j]) (M4) of the Virtual 3D Object that is easily followed/tracked by the human Eye (H2) under the control of the human Brain (H3).

The primary output of the Camera Trajectory Control function (F7) is the GOPD's next iteration's Actual Camera State ($C_{ActCam\_Obj}$) (M17), in particular the Independent Camera State Variables (M17.1), for subsequent use by the 2D Image Generator function (F1).

The operational goals of the Camera Trajectory Control function (F7) are to:
a. continually move the Virtual Video Camera (H7) from its Actual Camera State ($C_{ActCam\_Obj}$) (M17) (where it arrived from the GOPD's prior-iteration control activity) toward the newly computed Target Camera State ($C_{TargCam\_Obj}$) (M21) (where the camera would eventually end up if the User's Designated Object Point ($P_{DesigPt\_Obj}$) (M13) remained constant at its current value over subsequent control-loop time sample periods),
b. manipulate the Actual Camera State ($C_{ActCam\_Obj}$) (M17) so the image of the User's Designated Object Point ($P_{DesigPt\_Obj}$) (M13) moves from its current location on the Display Window (H4.1) toward the Home Pixel ($i_{Home}$, $j_{Home}$) (M3),
c. control the current Zoom Condition to zoom in if the if the User's gazepoint has remained moderately fixed around a single point on the 3D Object or to zoom out if the recent gazepoint activity has varied significantly around the object surface, and
d. produce a stable yet timely motion of the camera image that optimally utilizes the Eye/Brain's (M2/M3) natural smooth-pursuit behavior to easily track/follow a point of interest while accomplishing the GOPD goal of centering and zooming in on the User's Designated Object Point ($P_{DesigPt\_Obj}$) (M13) of interest.

With regard to the 'natural-camera-motion' goal d), it is ergonomically important for a GOPD system to accommodate the human's natural mental and physical processes involved in visually watching or examining real, moving, 3D objects. To obtain an optimum visual perspective angle and range for viewing a real object, a person naturally moves his head and body in addition to moving his eyes within his head.

In GOPD systems, the movements of the Virtual Video Camera Platform (H7.1) play the equivalent role of positioning the eyes to optimally observe, evaluate and interpret the Virtual 3D Object ($S_{Obj\_Obj}$) (M1). Thus, in GOPD systems the head and body do not have to make the actual movements. Indeed, a key feature of GOPD system operation is that the Camera Trajectory Control Function (F7) substantially eliminates the need for head and body motion as the User looks around at a 3D object. Additionally, the Virtual Video Camera Platform movements may significantly exceed real human capabilities, as long as the motions allow the brain to 'feel' like a natural extension of the brain/body/eye experience.

Since the Virtual Video Camera Platform (H7.1) is simulated, it has no real motion limitations; it can go virtually anywhere at any speed with any angular field of view. However, while it would be possible for the Inner Camera Trajectory Control Loop (L2) to instantaneously move the Actual Camera State ($C_{ActCam\_Obj}$) (1117) to the Target Camera State ($C_{TargCam\_Obj}$) (M21), such jerky, high-speed actions would make it difficult for the User to visually follow the resulting GOPD display activity with his eyes.

Because natural body motions involve force (from muscles), mass and momentum, physiologists typically model basic body motion dynamics (i.e. acceleration, velocity and position) using the mathematics of time-based differential equations, whose time solutions for each state variable (position, velocity and acceleration) are computed as the time integral of its higher order derivative. To maintain a basic similarity between the dynamics of the GOPD's Virtual Video Camera Platform (H87.1) and the dynamics of natural human body motion, preferred GOPD implementations also employ time-based-differential-equation models to simulate the fundamental Virtual Video Camera Platform (H87.1) dynamics. Descriptions of first and second order time-integration models of the GOPD's Virtual Video Camera Platform (H87.1) follow.

Recall that the Camera Trajectory Control function (F7) controls the three Independent Camera State Variables (M17.1) of the Actual Camera State s ($C_{ActCam\_Obj}$) (M17):
a. the Camera Position ($P_{ActCam\_Obj}$) (M17.1.1),
b. the Camera Orientation Angle ($\Gamma_{ActCam\_Obj}$) (M17.1.2), and
c. the Camera FOV Angle ($\alpha_{CurCamFOV}$) (M17.1.3).

Also recall that the above sub-states are further comprised of multiple individual variables. Thus the overall camera state can be considered to consists K individual directly-controlled camera variables $u_k$, where the subscript k denotes the index of individual variable.

In one embodiment of the Camera Trajectory Control function (F7), each directly-controlled camera variable $u_k$ has its own separate control loop. While the control logic is the same for each variable, the values of the control parameters (in this case the Camera Velocity Control Time Constants $T_{CamVel}[k]$ (M23)) may be different to accommodate the operational dynamics of each variable.

FIG. 7 shows a simple, "first order integration" model for controlling a control variable $u_k$. This algorithm achieves the above Camera Trajectory Control function (F7) goals by executing the following steps at each GOPD iteration sample. It:
a. computes a Camera State Error ($C_{CamError\_Obj}$) (M22) equal to the difference between the current Target Camera State ($C_{TargCam\_Obj}$) (M21) and the Actual Camera State ($C_{ActCam\_Obj}$) (M17),
b. sets a Camera State Velocity command ($V_{ActCam\_Obj}$) (M24) proportional to the Camera State Error ($C_{CamError\_Obj}$) (M22), c. limits the Camera State Velocity command ($V_{ActCam\_Obj}$) (M24) to a Camera Velocity Limit ($V_{CamLimit\_Obj}$) (M24.1) to prevent excessive rates for the GOPD User's eye to follow, d. computes a Camera State Increment ($\Delta C_{CamState\_Obj}$) (M26) equal to the Camera State Velocity ($V_{ActCam\_Obj}$) (M24) times the sample interval $\Delta T$, and e. moves the Virtual Video Camera (H7) to its next-frame state: the next iteration's Actual Camera State ($C_{ActCam\_Obj}$) (M17) is computed by adding the Camera State Increment ($\Delta C_{CamState\_Obj}$) (M26) to the now old Actual Camera State ($C_{ActCam\_Obj}$) (M17). (Note: steps d) and e) implement the time integration of the camera velocity to compute the camera position.)

In FIG. 7 the symbol $u_k(t_n)$ designates the $k^{th}$ individual directly-controlled camera variable within the overall Actual Camera State ($C_{ActCam\_Obj}$) (M17), and $t_n$ and $t_{n+1}$ indicate the times of the current and next GOPD sample iterations. The input to the Camera Trajectory Control function (F7) is the current, just computed ($t_n$) value of the Target Camera State ($C_{TargCam\_Obj}$) (M21). The output from the Camera Trajectory Control function (F7) is the next iteration's ($t_{n+1}$) value of the Actual Camera State ($C_{ActCam\_Obj}$) (M17).

A key part of the Camera Trajectory Control function (F7) design involves selecting appropriate values for the Camera Velocity Control Time Constants ($T_{CamVel}[k]$) (M23) to meet the operational 'natural-camera-motion' goal d) to match the eye/brain's natural smooth pursuit behavior.

As described in the function's step b) above, the Camera State Velocity command ($V_{ActCam\_Obj}$) (M24) is set to be proportional to the Camera State Error ($C_{CamError\_Obj}$) (M22), i.e.

$$\text{Velocity}[k] = \text{Error}[k]/\text{TimeConst}[k] \quad \text{(Eqn 3a)}$$

or $$V_{Cam}[k] = u_{k\_Error}/T_{CamVel}[k] \quad \text{(Eqn 3b)}$$

In accordance with this equation, larger errors produce larger camera velocities, and, correspondingly, smaller errors produce smaller camera velocities. Given a hypothetical step change in the target camera state, (where the target state moves instantaneously from one place to another, but then stays fixed at the new point as the camera trajectory unfolds), the camera trajectory plays out as follows:

The camera starts out moving at a speed proportional to the step size, (though possibly limited by step c)), But as the camera moves toward the "target" state, the error progressively decreases and the camera speed therefore also slows down as the target state is reached.

In control parlance, the shape of this time trajectory response to a step target command is a classic "first order exponential" response.

Among control system designers, a first order exponential response is sometimes criticized for never fully reaching its target. An alternative is to use a higher order trajectory model. A second order model, for example, can provide an equally fast overall response while at the same time providing a smoother response and an ability to fully reach its target.

Thus, a second order trajectory model is often preferred to a first order model.

While a first order model is specified by a single parameter T, a second order model has two parameters: a natural frequency $\omega$ and a damping coefficient $\zeta$ as opposed to a first order system's single parameter T. If an overall system response time of T is desired for a second order model, the parameters $\omega$ and $\zeta$ scan be set as follows:

$$\omega = 2\pi/T \quad \text{(Eqn 4a)}$$

and $$\zeta = 0.707 \quad \text{(Eqn 4b)}$$

For GOPD systems, the time constants should be set in accordance with the design principle of shifting the object display in a manner that the Eye/Brain (M2/M3) can easily, rapidly and stably track/follow the moving display of the Designated-Point Pixel ($i_{DesigPt}, i_{DesigPt}$) (M14) using its visual smooth pursuit mode of operation. Optimum values of these time constants typically vary between 2 and 5 seconds, but may vary considerably between different GOPD applications, depending on the User's current Eye/Brain capabilities, the complexity of the object being displayed, and the complexity of the underlying visual search task. A skilled control system designer, with a basic understanding of Eye/Brain dynamics, can find optimum time constant values with a combination of control theoretical analysis and human experimentation with the specific GOPD application.

GOPD's Coordinate Transformation Functions (F8.1 and F8.2)

To perform accurate and precise physical calculations in GOPD systems, it is necessary:

a. to express position, angular orientation and/or line data from several 3D objects or quantities within several different coordinate frames, and b. be able to convert position, orientation and/or line data between different coordinate frames.

Given the data for a specific transformation between 2 coordinate frames, the GOPD's general-purpose 3D Coordinate Transformation function (F8.1) converts position, vector or line data from either coordinate frame to the other. The 3D Coordinate Transformation function (F8.1) performs both forward and inverse transformations. 3D coordinate frame transformation functions are well known in mathematics and need no further explanation here.

The GOPD's Display-To-Pixel Transform function (F8.2) uses the Pixel Position array ($P_{PixPosn\_Disp}[i,j]$) (M2) to convert back and forth between 2D points (z=0) on the Display Device's (H4) display surface, expressed within the 3D Physical Display Coordinate Frame (R3), and the pixel index values [i,j] in the 2D Pixel Coordinate Frame (R5).

2D Image Generator Function (F1)

As discussed earlier, FIG. 3 shows an abstract geometric view of real and virtual GOPD objects along with relevant coordinate frames. For purposes of discussing the 2D Image Generator function (F1) here, the relevant objects and coordinate frame of FIG. 3 include:
the Virtual 3D Object (M1),
the Virtual Object Coordinate Frame (R1),
the Virtual Video Camera (H7),
the Virtual Camera Coordinate Frame (R2),
the Display Device (H4),
the Display Device Coordinate Frame (R3), and
the 2D Video Image (Q[i,j]) (M4).

The 2D Image Generator function (F1) has two primary inputs:

a. the new Actual Camera State ($C_{ActCam\_Obj}$) (M17) from the Camera Trajectory Control function (F7), and b. the GOPD's surface description of the Virtual 3D Object ($S_{Obj\_Obj}$) (M1), The 2D Image Generator function (F1) does two primary things:
  a. updates the Virtual-Object-To-Camera Coordinate Transform (VirtObjToCamTform) (M28) from the new Actual Camera State ($C_{ActCam\_Obj}$) (M17), and
  b. generates (or renders) the new 2D Video Image frame (Q[i,j]) (M4) to be displayed during the next GOPD iteration.

Procedures for rendering a 2D image of a virtual 3D object are well known in the Computer Graphics art.

Typically, such a rendering function loops through all the pixels in the image, calling a function that is here called the GetPixelColor function (F1.1), that:
  a. takes the pixel coordinate [i,j] as its input,
  b. computes the pixel's line-of-sight in the Virtual-Camera Coordinate Frame (R2),
  c. converts the pixel line-of-sight from the Virtual-Camera Coordinate Frame (R2) to the Virtual-Object Coordinate Frame (R1),
  d. projects the pixel line-of-sight, as expressed in the Virtual-Object Coordinate Frame (R1), out from the camera lens center to the first point (if any) where it intercepts the virtual object surface,
  e. uses the properties of that object surface point to determine the image pixel's color, and
  f. adds that pixel color to the image array.

Note: Steps b), c) and d) differ for Closeup-Capable Cameras and Infinite Distance Cameras. While the above descriptions for steps b), c) and d) aptly describe the image rendering for Closeup-Capable Cameras, where all pixel sight lines pass through the camera lens center point and diverge linearly as they approach the object, the image rendering for Infinite-Distance Cameras reduces to a simple linear projection of the object onto the camera image plane, where all the 'equivalent' pixel sight lines are mathematically treated as parallel.

(Recall: As discussed earlier in the section on the Object Point Lookup Function (F3), the above steps b), c) and d), which compute the underlying pixel line-of-sight geometry and find the line/object intercept, are identical to these steps done in the Object Point Lookup function (F3). The key difference between the two functions is that this GetPixelColor function (F1.1) returns the display color of the argument pixel [i,j], while the Object Point Lookup Function (F3) returns the object spatial position corresponding to the pixel).

Displaying the Next 2D Video Image Frame

In the final step of a GOPD iteration, the system copies the 2D Video Image (Q[i,j]) (M4) to the Display Device (H4) for the User (H1) to view and respond to in the next iteration.

GOPD System Initialization

Prior to beginning a GOPD run, the GOPD system typically:
  sets an initial value for the Actual Camera State ($C_{ActCam\_Obj}$) (M17), generally providing a full view of the Virtual 3D Object ($S_{Obj\_Obj}$) (M1),
  executes the 2D Image Generator function (F1) to set the initial 2D Video Image frame (Q[i,j]) (M4),
  displays the initial 2D Video Image frame (Q[i,j]) (M4) on the Display Device (H4), and
  initializes the Eyetracker Device (H5) operation.

Methods for Setting the Camera Target Control Parameters (M1.3)

A key part of any GOPD system design is the formulation of the Camera Target Control Parameters (M1.3) that specify how the camera should be positioned, oriented and zoomed as the User moves his Designated Object Point ($P_{DesigPt\_Obj}$) (M13) around the Virtual 3D Object ($S_{Obj\_Obj}$) (M1).

Recall that a separate set of Camera Target Control Parameters (M1.3) exists for each surface triangle in the Virtual 3D Object ($S_{Obj\_Obj}$) (M1), and that each triangle's set of Camera Target Control Parameters (M1.3) contains the following design parameters that define the desired Target Camera State ($C_{TargCam\_Obj}$) (M21) for the particular GOPD application:
  a. Camera Orientation Angle ($\Gamma_{TargCam\_Obj}$) (M1.3.1),
  b. Default Minimum Imaged Object Width ($W_{DfltMinImgWdth\_Obj}$) (M1.3.2),
  c. Default Maximum Imaged Object Width ($W_{DfltMaxImgWdth\_Obj}$) (M1.3.3), and
  d. Target Camera Distance ($D_{TargCamDist\_Obj}$) (M1.3.4).

Though the Camera Target Control Parameters (M1.3) could possibly be set manually (i.e. hard wired in the program), it is generally desirable that GOPD systems have a Set Target Camera Control Parameters function (F10) that automatically sets these detailed design parameters based on a set of higher-level control parameters discussed below. (Note: In a GOPD system where the Virtual 3D Object ($S_{Obj\_Obj}$) (M1) varies dynamically during GOPD runtime, an automated Set Camera Target Control Parameters function (F10) is required to keep up with the virtual model changes.)

Several alternative methods for a Set Camera Target Control Parameters function (F10) follow:
  Setting the Camera Orientation Angle ($\Gamma_{TargCam\_Obj}$) (M1.3.1)
  In general it is desirable for GOPD Users to view points on the Virtual 3D Object ($S_{Obj\_Obj}$) (M1) approximately 'straight on' toward the local surface profile. Thus, the Camera Orientation Angle ($\Gamma_{TargCam\_Obj}$) (M1.3.1) for each surface triangle can be set based on the Object Surface Normal Vectors (M1.2.4) in the neighborhood of the User's Designated Object Point ($P_{DesigPt\_Obj}$) (M13).

Additionally, it is desired to keep the Virtual Video Camera (H7) from moving (translating, rotating and/or zooming) too much in response to small changes in the User's Designated Object Point ($P_{DesigPt\_Obj}$) (M13). Thus it is not generally effective to simply set the Camera Orientation Angle ($\Gamma_{TargCam\_Obj}$) (M1.3.1) for each surface triangle equal to the normal vector for that triangle.

An effective way to stabilize camera motion as the User moves his gaze over small distances (e.g. from one triangle to another) is to program the Camera Target Control Parameters (M1.3) to vary the Camera Orientation Angle ($\Gamma_{TargCam\_Obj}$) (M1.3.1) smoothly over the object surface, despite what may be sharp local changes in the object surface itself. Here is a smoothing method for setting the Camera Orientation Angle ($\Gamma_{TargCam\_Obj}$) (M1.3.1):

Define the parameters of an 'influence sphere' within the Virtual 3D Object ($S_{Obj\_Obj}$) (M1) over which neighboring surface triangles have an influence on the current 'reference' triangle's Camera Orientation Angle ($\Gamma_{TargCam\_Obj}$) (M1.3.1). The sphere has an influence radius ($R_{OrientationInfluence}$) and a distance-dependent weighting profile $w_{dist}(r_{neighbor})$. The distance weighting profile $w_{dsti}(r_{neighbor})$ is highest at r=0, i.e. at the center of the reference triangle, and decays to zero as $r_{neighbor}$ approaches the edge at $R_{OrientationInfluence}$. A bell shaped distance weighting profile $w_{dsti}(r_{neighbor})$ is typically effective for smoothing the camera's viewing angle over locally 'rough' regions of object surface topology.

Cycle through each triangle in the Virtual 3D Object ($S_{Obj\_Obj}$) (M1), and:
  a. Define a neighbor weights $w_{neighbor}$ for each neighboring triangle within the influence sphere, including the reference triangle itself.
  b, Set each neighbor weight $w_{neighbor}$ as the product of the neighbor triangle area ($\alpha_{neighbor}$) and the neighbor's distance-dependent weight $w_{dist}(r_{neighbor})$:

$$w_{neighbor} = \alpha_{neighbor} * \text{profile } w_{dist}(r_{neighbor}) \quad (\text{Eqn 5})$$

c. Set the Camera Orientation Angle ($\Gamma_{TargCam\_Obj}$) (M1.3.1) for the reference triangle as the weighted average of the neighbors' Object Surface Normal Vectors (M1.2.4).

Setting the Default Minimum Imaged Object Width ($W_{DfltMinImgWdth\_Obj}$) (M1.3.2):

Recall that the Default Minimum Imaged Object Width ($W_{DfltMinImgWdth\_Obj}$) (M1.3.2) represents the maximum, i.e. narrowest, zoom condition that the camera reaches when the Camera Trajectory Control function (F7) finally settles the camera on a given Designated Object Point ($P_{DesigPt\_Obj}$) (M13).

In the simplest GOPD embodiments, the Default Minimum Imaged Object Widths ($W_{DfltMinImgWdth\_Obj}$) (M1.3.2 and M1.3.3) may be set to a constant value for all object triangles. In this case, the image magnification is the same whenever the GOPD system settles the camera on any virtual object point.

Another method is to decrease the zoom width over local object regions of higher surface complexity—on the assumption that higher surface complexity may indicate a need for closer viewing due to possible higher information density. One way to estimate surface complexity in the neighborhood of an object triangle is to compute variances in surface shape and/or color over an influence sphere around the triangle center.

Setting the Default Maximum Imaged Object Width ($W_{DfltMinImgWdth\_Obj}$) (M1.3.2):

Recall that the Default Maximum Imaged Object Width ($W_{DfltMinImgWdth\_Obj}$) (M1.3.2) represents the minimum, i.e. widest, camera zoom condition—which occurs at program startup and when the User looks all around the Virtual 3D Object ($S_{Obj\_Obj}$) (M1). Generally, there is no reason for the camera-image field of view to be larger than the full extent of the object. Thus, a simple and often adequate method for setting each triangle's Default Maximum Imaged Object Width ($W_{DfltMinImgWdth\_Obj}$) (M1.3.2) is to set them all to the overall maximum object extent.

A slightly more sophisticated method is to set each triangle's Default Maximum Imaged Object Width ($W_{DfltMinImgWdth\_Obj}$) (M1.3.2) to the maximum object extent visible by the camera when the camera is positioned at the current triangle's Camera Orientation Angle ($\Gamma_{TargCam\_Obj}$) (M1.3.1).

Setting the Target Camera Distance ($D_{TargCamDist\_Obj}$) (M1.3.4).

Recall that if the GOPD system has an Infinite-Distance Camera, or if the camera has a fixed (as opposed to variable) Camera FOV Angle ($\alpha_{TargCamFOV}$) (M21.3), the target Camera Distance ($D_{TargCamDist\_Obj}$) (M1.3.4) is not used in the Camera Target Control Parameters (M1.3) set. On the other hand, if the GOPD system has Closeup-Capable Camera with a controllable Camera FOV Angle ($\alpha_{..CamFOV}$) (M16.1.3), the set of Target Camera Distance parameters ($D_{TargCamDist\_Obj}$) (M1.3.4) must be set.

One method for setting the Target Camera Distance ($D_{TargCamDist\_Obj}$) (M1.3.4) is to set the distances for all the object triangles to a constant, causing the Target Camera State Calculator Function (F6) to always set the target camera position (expressed in the Target Camera State ($C_{TargCam\_Obj}$) (M21)) to be a fixed distance from the Designated Object Point ($P_{DesigPt\_Obj}$) (M13).

Another approach is to set the Camera Distance values ($D_{TargCamDist\_Obj}$) (M1.3.4) proportional to the Target Imaged Object Width ($W_{TargImgWdth\_Obj}$) (M22.2.2), thus providing an effectively constant Camera FOV Angle ($\alpha_{TargCamFOV}$) (M21.3) for all Designated Object Points ($P_{DesigPt\_Obj}$) (M13). (See Equation 2a.)

Treating Overlapping Surface Displays

When viewing a 2D display of a 3D object, there can be cases where the gaze line might intercept multiple overlapping surfaces on which the user may wish to designate his point of interest. For example, in the Pain Point application, when the user is looking at a point on the side of the torso, the view of the body may rotate around such that an arm moves in to impede the user's direct view of the torso point he was designating. Thus, when the user's gazeline, that has been tracking on a single surface, moves around and now encounters a nearer surface, a user friendly GOPD system should have an intelligent method for disambiguating which surface the designated object point should follow.

One method for selecting a tracked surface, when a gaze line that has been tracking on a single surface now encounters another, closer surface, is:

Normally, if the user's gazepoint on the original surface smoothly follows the originally designated object point on the original surface, the Designated Object Point Calculator function keeps the old more-distant surface as the tracked surface.

On the other hand, if the gazeline intersection with the new closer surface results from a large eye motion such as a saccade, indicating a significant shift in the user's attention point, the Designated Object Point Calculator function switches the tracked surface to the new, closer surface.

For some object types, it may be possible to avoid the occurrence of overlapping 3D surfaces in the 2D display by modifying the shape of the object online. An Object Shape Adjustment function in the GOPD system would anticipate that the gaze line is about to encounter a new, closer surface and change the geometry of the object to avoid that encounter. In the PainPoint application, for example, the Object Shape Adjustment function might move the limbs within the system's representation of the body object, e.g. to rotate an arm out of the way as the designated object point moves around the torso toward the arm.

When a gaze line does intercept overlapping surfaces of the displayed object, it is helpful to the user for the GOPD system to highlight the surface the designated object point is tracking. If the designated object point is on the first surface the gaze line intercepts, no special highlighting is required, since the 2D Image Generator function will not show the second surface. If, on the other hand, the designated object point is on the second surface, the image generator function may be programmed to fade out the display of the untracked surface and display the second surface. Similarly, when the gazeline leaves an untracked surface, the system un-fades the untracked surface.

Manual GOPD Controls

In many GOPD applications it is useful to have manual controls that augment the eye control of the object display.

In applications such as the PainPoint system where outside observers are involved, it is useful for the Observer (H8) to have manual control over the system operation. In the PainPoint application, for example, the Observer (H8) is typically a nurse, doctor or caregiver, and it is generally the Observer (H8) who has the primary control of the overall application operation. The Observer (H8) typically places the system in front of the patient, starts and stops the dynamic tracking operation, and has a variety of controls to interact with the patient as she/he gathers the needed medical information. For example, the Observer (H8) can pause/freeze the object display to verify with the patient that the currently designated point is the point he actually wishes to designate. During the pause period, the patient is free to move his gaze around while answering the question without the display responding.

In many GOPD applications it is desirable for either the User (H1) and/or the outside Observer (H8) to be able to move the Designated Object Point ($P_{DesigPt\_Obj}$) (M13) manually as well as visually. The location of the GOPD's designated point may be manually moved to a cursor location by clicking a mouse, trackpad or trackball.

Note: Though the chief GOPD applications described in this specification use eyegaze as their primary input to control the Virtual Video Camera (H7) view of a Virtual 3D Object (Sob obj) (M1), the general functionality of the GOPD architecture may be useful in many applications that do not use gaze input at all. For example, in the above case of an Operator (H9) manually moving the Designated Object Point ($P_{DesigPt\_Obj}$) (M13) by a single mouse click, the overall operation of the Outer Eye Control Loop (L1) and the Inner Camera Trajectory Control Loop (L2) causes the Virtual Video Camera (H7) to translate, rotate and zoom in manner that allows the User to easily follow the camera video path across the object surface, in turn allowing him to mentally keep track of the viewing context as the Virtual Video Camera (H7) moves from one Designated Object Point ($P_{DesigPt\_Obj}$) (M13) to another.

In some GOPD applications it may be desirable for the User (H1) and/or Observer (H8) to be able to manually override the GOPD system's default zoom limits during a GOPD session. In the PainPoint application for example, the Observer (H8) might want the system to temporarily allow more or less zoom in a local region of the body that the patient is currently looking at.

The following embodiment of a Adjust Zoom Limit function (F9) provides a simple, rapid way for an Operator (H9) to make such adjustments online during runtime. The method can be used for adjusting either the Current Minimum or Maximum Imaged Object Width ($W_{Cur..ImgWdth\_Obj}$) (M1.3.6 or M1.3.7).

Before continuing with the description of the Adjust Zoom Limit function (F9), recall that:

Because increased zoom factors result in smaller regions of the object being displayed, a maximum zoom limit is controlled by the Current Minimum Imaged Object Width ($W_{CurMinImgWdth\_Obj}$) (M1.4.3), and visa versa.

The Zoom Control function (F5) computes current zoom-limit widths as the sum of the default Imaged Object Width, which is constant, and the current Imaged Object Width adjustment, which is 0 at the beginning of a GOPD session and varies under manual control:

$$\text{Current..Width} = \text{Default..Width} + \text{..Width Adjustment} \quad \text{(Eqn 6)}$$

Consecutive width adjustments accumulate during a GOPD session.

The zoom limits should vary smoothly over the Virtual 3D Object surface ($S_{Obj\_Obj}$) (M1) to minimize dynamic zoom variation when the Designated Object Point ($P_{DesigPt\_Obj}$) (M13) moves small distances on the object.

Let's first take the case of allowing an Operator (H9) to adjust the maximum zoom limit, i.e. to adjust the Current Minimum Imaged Object Width ($W_{CurMinImgWdth\_Obj}$) (M1.4.3). An operator may wish to adjust the maximum zoom when:

a. the User has fairly well designated a specific object point,
b. the system has zoomed in to the Current Minimum Imaged Object Width ($W_{CurMinImgWdth\_Obj}$) (M1.4.3) for that designated point, and
c. the Operator (H9), based on what he sees at the moment, wishes either to allow the system to zoom in more or to force it to zoom out some.

The Adjust Zoom Limit function (F9) function utilizes two buttons for the Operator (H9) to click:

The Zoom In command allows the GOPD system to zoom in further if the User's gaze is sufficiently still, and the Zoom Out command causes the system to widen out the field of view despite a still User gaze.

The following is a preferred method for the Adjust Zoom Limit function (F9) operation:

The function first checks to see if the current zoom state is at (or very near) its limit. If the system is not currently at the zoom limit, the command is ignored because the results of a change would not be observed at that time. (Ignoring zoom-limit adjustment commands when the system is not currently at a limit minimizes the adverse effects of unintended zoom adjustment clicks when the results of those commands could not be observed.) Otherwise, if the system is at the limit, the function executes the following limit modifications.

The Minimum Imaged Object Width Adjustment ($W_{MinImgWdthAdj\_Obj}$) (M1.4.3) is adjusted for all the object Object-Surface Triangles (M1.2) within a vicinity of the current Designated Object Point ($P_{DesigPt\_Obj}$) (M13), e.g. within a circle of radius $R_{ZoomAdjScope}$.

The magnitude $G(R_{Triangle})$ for each triangle's zoom adjustment varies gradually over the circle, with a value $G_0$ at the center of the circle and decreasing along a bell-shaped curve to zero as the triangle distance $R_{Triangle}$ increases toward $R_{ZoomAdjScope}$. The bell-shaped $G(R_{Triangle})$ curve maintains the GOPD design property that zoom limits vary smoothly over the Virtual 3D Object surface ($S_{Obj\_Obj}$) (M1).

$G_0$ and $G(R_{Triangle})$ are unitless, proportionality scale factors that control the magnitude of the new Width-Limit Increment to be made on the current call to the Adjust Zoom Limit function (F9).

$G_0$ is negative for Zoom-In commands and positive for Zoom-Out commands. Thus, Zoom-In commands increase the effective zoom factor by decreasing the Minimum Imaged Object Width Correction ($W_{MinImgWdthAdj\_Obj}$) (M1.4.2), and the converse holds for Zoom-Out commands.

The value for the new Width-Limit Increment is proportional to the current width limit:

$$\textit{new } \text{Width-Limit Increment} = G(R_{Triangle}) * \text{Current Width Limit} \quad \text{(Eqn 7)}$$

The updated value of the Width-Limit Adjustment is the sum of the prior Width-Limit Adjustment and the new Width-Limit Increment:

$$\text{updated Width-Limit Adjustment} = \text{prior Width-Limit Adjustment} + \textit{new } \text{Width-Limit Increment} \quad \text{(Eqn 8)}$$

(For example if $G_0$ is 0.02, $R_{Triangle}$ is 0, the current width limit for an object surface triangle is 1.0 cm, and the User hits the Zoom In key, the new Width-Limit Adjustment is −2% of 1 cm=−0.02 cm, and the updated Width-Limit Adjustment is 1.0 cm−0.02 cm=0.98 cm. So the zoom factor is up 2% and the corresponding zoom width is 2% smaller— for the triangle at the center of the adjustment region.)

The constants $G_0$ and $R_{ZoomAdjScope}$, and the bell-curve parameters for the $G(R_{Triangle})$ function, are set by the GOPD designer to meet the needs of the specific GOPD application.

Though a call to the Adjust Zoom Limit function (F9) instantaneously changes the profile of the Current Minimum Imaged Object Width ($W_{CurMinImgWdth\_Obj}$) (M1.4.3) for all the surface Object-Surface Triangles (M1.2) in the local vicinity of the Designated Object Point ($P_{DesigPt\_Obj}$) (M13), the GOPD's overall dynamic response to the change is more gentle. In reaction to a zoom limit command:
   a. The Target Camera State Calculator function (F5) instantaneously modifies the Target Camera State ($C_{TargCam\_Obj}$) (M21).
   b. The Camera Trajectory Control function (F6) begins to smoothly adjust the camera trajectory to move toward the new zoom limit, and
   c. The Operator (H9) can see the results of his zoom modification and decide to repeat the zoom increment, reverse it, or leave it alone.

In many GOPD applications it is desirable to allow an Operator (H9) to manually designate a point on the 3D surface. The following manual point designation method employs a conventional mouse and curser:

The GOPD system begins in a 'static' manual state, where the automatic Camera Trajectory Control function (F7) is de-activated, i.e. the image display remains still, independent of the cursor location on the screen. In the static manual state, the User is free to move the mouse around the screen while the object display remains still.

When an Operator (H9) clicks the mouse, the GOPD system sets the Gazepoint Pixel variable ($i_{GazePt\_Pix}$, $j_{GazePt\_Pix}$) (M11) to the current cursor location, computes a new Designated Object Point ($P_{DesigPt\_Obj}$) (M13), and switches the system to the 'active' manual state.

In the 'active' manual state, the system resumes its iterative operation where the Camera Trajectory Control function (F7) drives the camera to view the new Designated Object Point ($P_{DesigPt\_Obj}$) (M13)—with its appropriate motion dynamics (goal d) that allow the user to easily watch/track the motion of the designated point in the display.

The system remains in the active state until:
   a) the control loop slows to stop on its own, or
   b) the User clicks the mouse again, at which point the system switches back to the 'static' manual state.

Other GOPD Applications

In addition to the PainPoint application, the GOPD concept has significant potential use in other fields such as education, virtual reality displays, video gaming, security, surveillance, mapping, search and rescue, and robotics.

In education for example, GOPD systems allow people to visually explore physical and geographical objects and scenes. The Virtual 3D Object ($S_{Obj\_Obj}$) (M1) is the equivalent of a digital twin which a person can easily visually examine from multiple perspectives.

GOPD Use with Physical Cameras

The fundamental GOPD architecture can be extended to employ real as well as virtual video cameras. A real Physical Video Camera may, for example, be mounted on a physical platform such as a drone and be controlled to move around in real space with a position, angular orientation and/or zoom state that follows the corresponding position, orientation and/or zoom of the Virtual Video Camera (H7) in the GOPD's virtual space. The Camera Trajectory Control function (F7) simultaneously controls both the Virtual Video Camera (H7) and the real Physical Video Camera. As the GOPD Operator (H9) drives the Virtual Video Camera (H7) within the Virtual Object Coordinate Frame (F1), the GOPD system automatically controls the real Physical Video Camera to perform corresponding maneuvers in real space.

Unlike purely virtual GOPD systems where the Virtual Video Camera (H7) may be moved without limits, the Camera Trajectory Control function (F7) for GOPD systems with real Physical Video Cameras mounted on real platforms must be designed to accommodate the physical dynamics of the camera and platform equipment.

Using geometrical construction methods for synthesizing 3D digital twin models from a set of 2D images, the video data captured by the real Physical Video Camera may be used to update the GOPD's Virtual 3D Object ($S_{Obj\_Obj}$) (M1). Many 3D model synthesizers exist today that can operate either ex post facto or online in real time.

Additionally, the sensor devices in physical cameras use in GOPD systems need not be limited to traditional optical video cameras. The GOPD concept may be used with any imaging sensor device, including for example radar, sonar and heat maps, that produces a 2D or 3D image of an object or scene.

GOPD System Implementation

Returning to FIG. 3, this figure shows a system for controlling the display of a 3D object or scene on a two-dimensional 2D display device, in accordance with various embodiments. The system includes processor 310. Processor 310 represents just one of one or more processors that can be used in various embodiments. Processor 310 can be, but is not limited to, a controller, a computer, a microprocessor, the computer system of FIG. 1, or any device capable of analyzing data. Processor 310 can also be any device capable of sending and receiving control signals and data. Processor 310 can be a processor of eyetracking device H6 or can be a separate device.

Processor 310 calculates a 3D mathematical model surface M1 of an object or scene from a plurality of 3D points on surface M1. Processor 310 generates a 2D image M4 of surface M1 from a virtual camera H7. A target virtual camera state of virtual camera H7 includes values for a plurality of camera control and location parameters. Processor 310 calculates a target virtual camera state for each surface point of the plurality of 3D points on surface M1.

In various embodiments, the target virtual camera state includes a set of camera orientation angles that prescribe a desired orientation for virtual camera H7 to view a point on surface M1.

In various embodiments, values for the set of camera orientation angles are computed from a surface normal vector at a point, or as a weighted average of surface normal vectors in the local neighborhood of the point.

In various embodiments, the target virtual camera state comprises a set of camera zoom limit conditions that prescribe a minimum and a maximum camera zoom condition for the virtual camera to view a point on surface M1.

In various embodiments, values for the set of camera zoom limit conditions are adjusted by an operator.

In various embodiments, the set of camera zoom limit conditions includes a width of an area of surface M1 that is displayed when a point on surface M1 is viewed.

In various embodiments, the target virtual camera state includes a set of camera distances that prescribes one or more distances from virtual camera H7 to a point on surface M1 to view the point on surface M1.

In various embodiments, the target virtual camera state includes an angular field of view for virtual camera H7.

In various embodiments, a value for the angular field of view is computed from a virtual camera distance and a view width.

In various embodiments, processor 310 further displays on a 2D display device M4 an initial image of the surface as shown from virtual camera H7 using an initial virtual camera state.

In various embodiments, processor 310 further iteratively displays on 2D display device M4 successive images of surface M1 as produced by virtual camera H7 using successive virtual camera states.

In various embodiments, processor 310 performs a number of additional steps. In a step (I), processor 310 receives from a user a 2D user-designated display coordinate on 2D display device M4. In a step (J), processor 310, calculates a 3D user-designated object point on surface M1 corresponding to the 2D user-designated display coordinate on 2D display device M4. In a step (K), processor 310, determines a next virtual camera state corresponding to one or more of the most recently computed 3D user-designated object points. In a step (L), processor 310, virtually moves a current virtual camera state toward the next virtual camera state. In a step (M), processor 310 generates a next image for display on 2D display device M4 based on the next virtual camera state.

In various embodiments, in step (K), the next virtual camera state is determined from a smoothed average of two or more receding 3D user-designated object points.

In various embodiments, processor 310 further, in a step (N), iteratively performs steps I-M until the next virtual camera state is equivalent to a target virtual camera state of a surface point of surface M1 within a set of target tolerance values or until steps i-m are stopped by an operator.

In various embodiments, the user selects the user-designated display coordinate by manually placing a cursor on 2D display device M4 and the user-designated display coordinate is received through the use of a pointing device (not shown).

In various embodiments, the user selects the user-designated display coordinate by looking at a point on 2D display device M4 and the user-designated display coordinate is received through the use of eyetracking device H6.

In various embodiments, processor 310 further makes adjustments to the next virtual camera state with dynamics based on time-based differential equations, thereby facilitating a human eye, under the control of a human brain, to visually track or follow the motion of the designated imaged point object point on 2D display device M4 as virtual camera H7 translates, rotates, or zooms.

In various embodiments, processor 310 further limits velocities of the next virtual camera state.

In various embodiments, the next virtual camera state includes a view width of an area of surface M1 and processor 310 further calculates a value for the view width of an area of surface M1 that is proportional to the magnitude of a variation of a user's gazepoint across surface M1 calculated from two or more gazepoints received from eyetracking device H6.

GOPD Method Implementation

Figure 8:
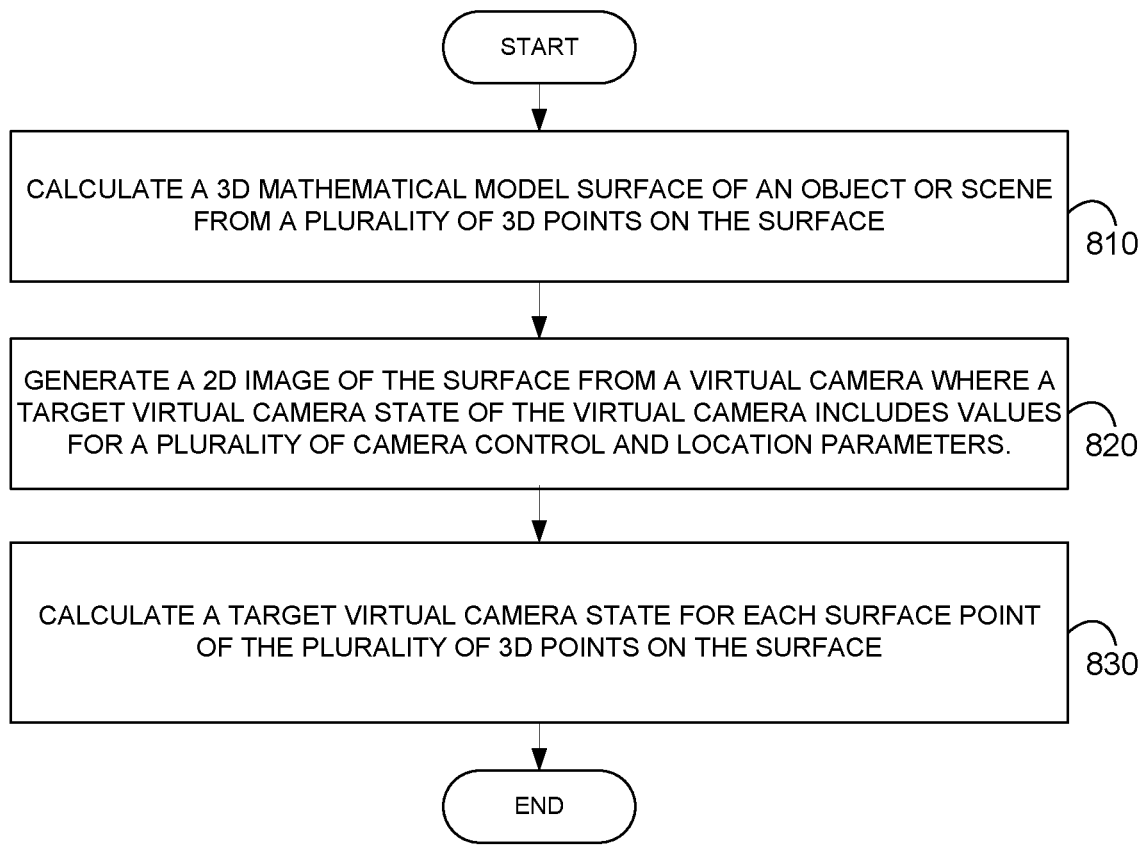
FIG. 8 is an exemplary flowchart showing a method for controlling the display of a 3D object or scene on a 2D display device, in accordance with various embodiments.

FIG. 8 is an exemplary flowchart showing a method 800 for controlling the display of a 3D object or scene on a 2D display device, in accordance with various embodiments.

In step 810 of method 800, a 3D mathematical model surface of an object or scene from a plurality of 3D points on the surface is calculated.

In step 820, a 2D image of the surface from a virtual camera is generated. A target virtual camera state of the virtual camera includes values for a plurality of camera control and location parameters.

In step 830, a target virtual camera state is calculated for each surface point of the plurality of 3D points on the surface.

GOPD Computer Program Product

In various embodiments, a computer program product includes a non-transitory tangible computer-readable storage medium whose contents include a program with instructions being executed on a processor so as to perform a method for controlling the display of a 3D object or scene on a 2D display device. This method is performed by a system that includes one or more distinct software modules.

Figure 9:
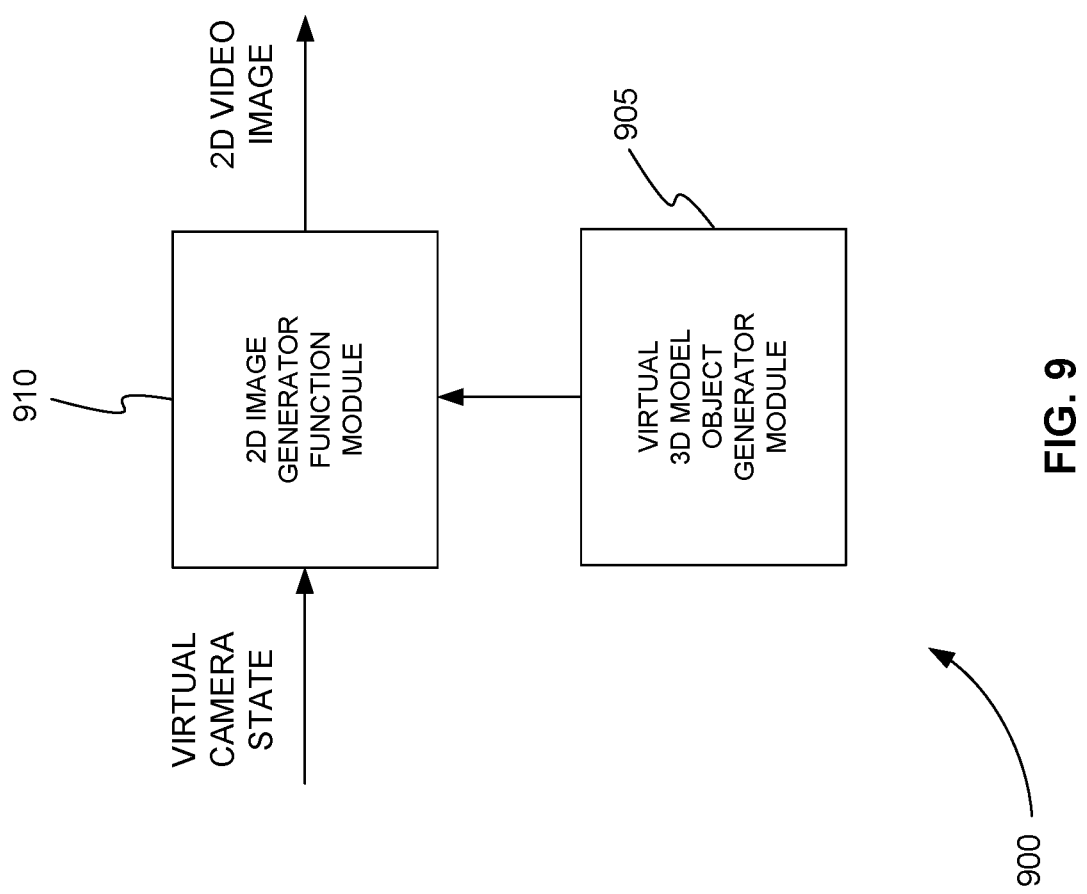
FIG. 9 is a schematic diagram of a system that includes one or more distinct software modules and that performs a method for controlling the display of a 3D object or scene on a 2D display device, in accordance with various embodiments.

FIG. 9 is a schematic diagram of a system 900 that includes one or more distinct software modules and that performs a method for controlling the display of a 3D object or scene on a 2D display device, in accordance with various embodiments. System 900 includes a virtual 3D model object generator module 905 and 2D image generator function 910.

3D model object generator module 905 calculates a 3D mathematical model surface of an object or scene from a plurality of 3D points on the surface. 2D image generator function 910 generates a 2D image of the surface from a virtual camera. A target virtual camera state of the virtual camera includes values for a plurality of camera control and location parameters. 2D image generator function 910 calculates a target virtual camera state for each surface point of the plurality of 3D points on the surface.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A method for controlling the display of a three-dimensional (3D) object or scene on a two-dimensional (2D) display device, comprising:
(a) calculating a 3D mathematical model surface of an object or scene from a plurality of 3D points on the surface,
(b) generating a 2D image of the surface from a virtual camera, wherein a target virtual camera state of the virtual camera comprises values for a plurality of camera control and location parameters, (c) calculating a target virtual camera state for each surface point of the plurality of 3D points on the surface, (d) displaying on a 2D display device an initial image of the surface as shown from the virtual camera using an initial virtual camera state, (e) iteratively displaying on the 2D display device successive images of the surface as produced by the virtual camera using successive virtual camera states, (f) receiving from a user a 2D user-designated display coordinate on the 2D display device, (g) calculating a 3D user-designated object point on the surface corresponding to the 2D user-designated display coordinate on the 2D display device, (h) determining a next virtual camera state corresponding to one or more of the most recently computed 3D user-designated object points, (i) virtually moving a current virtual camera state toward the next virtual camera state, and (j) generating a next image for display on the 2D display device based on the next virtual camera state.

2. The method of claim 1, wherein, in step au, the next virtual camera state is determined from a smoothed average of two or more receding 3D user-designated object points.

3. The method of claim 1, further comprising (k) iteratively performing steps i-m until the next virtual camera state is equivalent to a target virtual camera state of a surface point on the surface within a set of target tolerance values or until steps i-m are stopped by an operator.

4. The method of claim 1, wherein the user selects the user-designated display coordinate by manually placing a cursor on the 2D display device and the user-designated display coordinate is received through the use of a pointing device.

5. The method of claim 1, wherein the user selects the user-designated display coordinate by looking at a point on the 2D display device and the user-designated display coordinate is received through the use of an eyetracking device.

6. The method of claim 1, further comprising making the iterative adjustments to the next virtual camera state with dynamics based on time-based differential equations, thereby facilitating a human eye, under the control of a human brain, to visually track or follow the motion of the designated imaged point object point on the 2D display device as the virtual camera translates, rotates, or zooms.

7. The method of claim 6, further comprising limiting velocities of the next virtual camera state.

8. The method of claim 4, wherein the next virtual camera state comprises a view width of an area of the surface and further comprising calculating a value for the view width of an area of the surface that is proportional to the magnitude of a variation of a user's gazepoint across the surface calculated from two or more gazepoints received from the eyetracking device.

* * * * *

UNITED STATES PATENT AND TRADEMARK OFFICE
CERTIFICATE OF CORRECTION

PATENT NO. : 11,849,098 B2
APPLICATION NO. : 18/318219
DATED : December 19, 2023
INVENTOR(S) : Cleveland et al.

It is certified that error appears in the above-identified patent and that said Letters Patent is hereby corrected as shown below:

In the Claims

Column 43, Line 24 (Claim 2), "step au" should read --step (h)--

Column 43, Line 26 (Claim 2), "receding" should read --preceding--

Column 43, Line 28 (Claim 3) and Column 44, Line 2 (Claim 3), each occurrence, "steps i-m" should read --steps (f)-(j)--

Signed and Sealed this
Eighth Day of October, 2024

Katherine Kelly Vidal
*Director of the United States Patent and Trademark Office*